US006465185B1

United States Patent
Goldfine et al.

(10) Patent No.: US 6,465,185 B1
(45) Date of Patent: Oct. 15, 2002

(54) POLYMORPHIC HUMAN PC-1 SEQUENCES ASSOCIATED WITH INSULIN RESISTANCE

(75) Inventors: Ira Goldfine, San Francisco, CA (US); Vincenzo Trischitta, San Giovanni Rotondo (IT); Riccardo Vigneri, Catania (IT); Antonio Pizzuti, San Giovanni Rotondo (IT); Lucia A. Frittitta, Catania (IT)

(73) Assignees: Instituto di Ricovero e Cura a Carattere Scientifico, Foggia (IT); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/438,906

(22) Filed: Nov. 18, 1999

Related U.S. Application Data

(60) Provisional application No. 60/108,853, filed on Nov. 18, 1998.

(51) Int. Cl.[7] .............................. C12Q 1/68; C07H 21/04
(52) U.S. Cl. .......................... 435/6; 536/23.1; 536/24.3; 536/24.33; 536/24.31
(58) Field of Search .............................. 435/6; 536/23.1, 536/24.31, 24.33, 24.3

(56) References Cited

PUBLICATIONS

Buckley et al. Genbank Accession No. M57736, Mar. 1995.*
Hillier et al. Genbank Accession No. N94942, Apr. 1996.*
Trischitta et al. "Early molecular defects in human insulin resistance" Diabetes Met. vol. 13, No. 3, p. 147–162, 1997.*
Whitehead et al. "Expression of the putative inhibitor of the insulin receptor tyrosine kinase PC-1 in dermal fibroblasts from patients with syndromes of severe insulin resistance" Clin. Endocrin. vol. 47, p. 65–70, Jul. 1997.*
Rasmussen et al. "The K121Q variant of the human PC-1 gene is note associated with insulin resistance" Diabetes, vol. 49, p. 1608–1611, Sep. 2000.*
Accession No. AA621565.
Accession No. AI090484.
Accession No. D12485 and DO1250.
Accession No. M57736 and J05654.
Argolias, A., et al., "Role of PC-1 Gene Polymorphism (K121Q) in the Progression of Renal Disease in Type 1 Diabetic Pateients," *Diabetologia* (Aug. 1999) vol. 42:A267.
Belli, et al., "Identification and Characterization of a Soluble Form of the Plasma Cell Membrane Glycoprotein PC-1 (5'–nucelotide phosphodiesterase)," *J. Biochem* (1993) vol.217:421–428.
Frittitta, L., et al., "K121Q Polymorphism in Exon 4 of PC-1 Gene is Strongly Associated With Insulin Resistance," *Diabetologia* (Aug. 1999) vol. 42:A20.
Frittitta, Lucia, et al., "Elevated PC-1 Content in Cultured Skin Fibroblasts Correlates With Decreased In Vivo and In Vitro Insulin Action in Nondiabetic Subjects," *Diabetes* (Jul. 1998) vol. 47:1095–1100.
Goldfine, Ira D., et al., "Membrane Glycoprotein PC-1 and Insulin Resistance," *Molecular and Cellular Biochemistry* (1988) vol. 182:177–184.
Pizzuti, Antonio, et al., "A Polymorphism (K121Q) of the Human Glycoprotein PC-1 Gene Coding Is Strongly Associated With Insulin Resistance," *Diabetes* (Sep. 1999) vol. 48:1881–1884.
Reaven, Gerald M., "Role of Insulin Resistance in Human Disease," *Diabetes* (Dec. 1988) vol. 37:1595–1607.

* cited by examiner

*Primary Examiner*—W. Gary Jones
*Assistant Examiner*—Jeanine Goldberg
(74) *Attorney, Agent, or Firm*—Pamela J. Sherwood; James S. Keddie; Bozicevic, Field & Francis LLP

(57) ABSTRACT

A novel polymorphism in the human PC-1 gene is characterized, which is associated with an increased predisposition to developing insulin resistance. The polymorphism affects heterozygous and homozygous carriers of the allele. The subject nucleic acids and fragments thereof, encoded polypeptides, and antibodies specific for the polymorphic amino acid sequence are useful in determining a genetic predisposition to insulin resistance. The encoded protein is useful in drug screening for compositions that affect the activity of PC-1 and insulin receptor activity or expression.

3 Claims, 3 Drawing Sheets

SEQUENCE LISTING

```
<160> NUMBER OF SEQ ID NOS: 35

<210> SEQ ID NO 1
<211> LENGTH: 3486
<212> TYPE: DNA
<213> ORGANISM: H. sapiens
<220> FEATURE:
<221> NAME/KEY: CDS
<222> LOCATION: (164)...(2785)

<400> SEQUENCE: 1
ggccacgatg gagcgcgacg gctgcgcggg gggcgggagc cgcggcggcg agggcgggcg         60
cgctccccgg gagggcccgg cggggaacgg ccgcgatcgg ggccgcagcc acgctgccga        120
ggcgcccggg gacccgcagg cggccgcgtc cttgctggcc cct atg gac gtg ggg         175
                                                Met Asp Val Gly
                                                 1 gag gag ccg ctg gag aag gcg gcg cgc gcc cgc act gcc aag gac ccc         223
Glu Glu Pro Leu Glu Lys Ala Ala Arg Ala Arg Thr Ala Lys Asp Pro
 5                  10                  15                  20 aac acc tat aaa gta ctc tcg ctg gta ttg tca gta tgt gtg tta aca         271
Asn Thr Tyr Lys Val Leu Ser Leu Val Leu Ser Val Cys Val Leu Thr
                25                  30                  35 aca ata ctt ggt tgt ata ttt ggg ttg aaa cca agc tgt gcc aaa gaa         319
Thr Ile Leu Gly Cys Ile Phe Gly Leu Lys Pro Ser Cys Ala Lys Glu
            40                  45                  50 gtt aaa agt tgc aaa ggt cgc tgt ttc gag aga aca ttt ggg aac tgt         367
Val Lys Ser Cys Lys Gly Arg Cys Phe Glu Arg Thr Phe Gly Asn Cys
        55                  60                  65 cgc tgt gat gct gcc tgt gtt gag ctt gga aac tgc tgt tta gat tac         415
Arg Cys Asp Ala Ala Cys Val Glu Leu Gly Asn Cys Cys Leu Asp Tyr
    70                  75                  80
```

-continued

| | |
|---|---|
| cag gag acg tgc ata gaa cca gaa cat ata tgg act tgc aac aaa ttc<br>Gln Glu Thr Cys Ile Glu Pro Glu His Ile Trp Thr Cys Asn Lys Phe<br>85                               90                          95                      100 | 463 |
| agg tgt ggt gag aaa agg ttg acc aga agc ctc tgt gcc tgt tca gat<br>Arg Cys Gly Glu Lys Arg Leu Thr Arg Ser Leu Cys Ala Cys Ser Asp<br>                          105                       110                       115 | 511 |
| gac tgc aag gac aag ggc gac tgc tgc atc aac tac agt tct gtg tgt<br>Asp Cys Lys Asp Lys Gly Asp Cys Cys Ile Asn Tyr Ser Ser Val Cys<br>120                               125                           130 | 559 |
| caa ggt gag aaa agt tgg gta gaa gaa cca tgt gag agc att aat gag<br>Gln Gly Glu Lys Ser Trp Val Glu Glu Pro Cys Glu Ser Ile Asn Glu<br>                          135                       140                       145 | 607 |
| cca cag tgc cca gca ggg ttt gaa acg cct cct acc ctc tta ttt tct<br>Pro Gln Cys Pro Ala Gly Phe Glu Thr Pro Pro Thr Leu Leu Phe Ser<br>150                             155                           160 | 655 |
| ttg gat gga ttc agg gca gaa tat tta cac act tgg ggt gga ctt ctt<br>Leu Asp Gly Phe Arg Ala Glu Tyr Leu His Thr Trp Gly Gly Leu Leu<br>165                             170                       175                       180 | 703 |
| cct gtt att agc aaa cta aaa aaa tgt gga aca tat act aaa aac atg<br>Pro Val Ile Ser Lys Leu Lys Lys Cys Gly Thr Tyr Thr Lys Asn Met<br>                          185                       190                       195 | 751 |
| aga ccg gta tat cca aca aaa act ttc ccc aat cac tac agc att gtc<br>Arg Pro Val Tyr Pro Thr Lys Thr Phe Pro Asn His Tyr Ser Ile Val<br>                          200                       205                       210 | 799 |
| acc gga ttg tat cca gaa tct cat ggc ata atc gac aat aaa atg tat<br>Thr Gly Leu Tyr Pro Glu Ser His Gly Ile Ile Asp Asn Lys Met Tyr<br>                          215                       220                       225 | 847 |
| gat ccc aaa atg aat gct tcc ttt tca ctt aaa agt aaa gag aaa ttt<br>Asp Pro Lys Met Asn Ala Ser Phe Ser Leu Lys Ser Lys Glu Lys Phe<br>230                             235                       240 | 895 |
| aat cct gag tgg tac aaa gga gaa cca att tgg gtc aca gct aag tat<br>Asn Pro Glu Trp Tyr Lys Gly Glu Pro Ile Trp Val Thr Ala Lys Tyr<br>245                             250                       255                       260 | 943 |
| caa ggc ctc aag tct ggc aca ttt ttc tgg cca gga tca gat gtg gaa<br>Gln Gly Leu Lys Ser Gly Thr Phe Phe Trp Pro Gly Ser Asp Val Glu<br>                          265                       270                       275 | 991 |
| att aac gga att ttc cca gac atc tat aaa atg tat aat ggt tca gta<br>Ile Asn Gly Ile Phe Pro Asp Ile Tyr Lys Met Tyr Asn Gly Ser Val<br>                          280                       285                       290 | 1039 |
| cca ttt gaa gaa agg att tta gct gtt ctt cag tgg cta cag ctt cct<br>Pro Phe Glu Glu Arg Ile Leu Ala Val Leu Gln Trp Leu Gln Leu Pro<br>                          295                       300                       305 | 1087 |
| aaa gat gaa aga cca cac ttt tac act ctg tat tta gaa gaa cca gat<br>Lys Asp Glu Arg Pro His Phe Tyr Thr Leu Tyr Leu Glu Glu Pro Asp<br>310                             315                       320 | 1135 |
| tct tca ggt cat tca tat gga cca gtc agc agt gaa gtc atc aaa gcc<br>Ser Ser Gly His Ser Tyr Gly Pro Val Ser Ser Glu Val Ile Lys Ala<br>325                             330                       335                       340 | 1183 |
| ttg cag agg gtt gat ggt atg gtt ggt atg ctg atg gat ggt ctg aaa<br>Leu Gln Arg Val Asp Gly Met Val Gly Met Leu Met Asp Gly Leu Lys<br>                          345                       350                       355 | 1231 |
| gag ctg aac ttg cac aga tgc ctg aac ctc atc ctt att tca gat cat<br>Glu Leu Asn Leu His Arg Cys Leu Asn Leu Ile Leu Ile Ser Asp His<br>                          360                       365                       370 | 1279 |
| ggc atg gaa caa ggc agt tgt aag aaa tac ata tat ctg aat aaa tat<br>Gly Met Glu Gln Gly Ser Cys Lys Lys Tyr Ile Tyr Leu Asn Lys Tyr<br>                          375                       380                       385 | 1327 |
| ttg ggg gat gtt aaa aat att aaa gtt atc tat gga cct gca gct cga<br>Leu Gly Asp Val Lys Asn Ile Lys Val Ile Tyr Gly Pro Ala Ala Arg<br>390                             395                       400 | 1375 |

```
ttg aga ccc tct gat gtc cca gat aaa tac tat tca ttt aac tat gaa      1423
Leu Arg Pro Ser Asp Val Pro Asp Lys Tyr Tyr Ser Phe Asn Tyr Glu
405                 410                 415                 420 ggc att gcc cga aat ctt tct tgc cgg gaa cca aac cag cac ttc aaa      1471
Gly Ile Ala Arg Asn Leu Ser Cys Arg Glu Pro Asn Gln His Phe Lys
                425                 430                 435 cct tac ctg aaa cat ttc tta cct aag cgt ttg cac ttt gct aag agt      1519
Pro Tyr Leu Lys His Phe Leu Pro Lys Arg Leu His Phe Ala Lys Ser
            440                 445                 450 gat aga att gag ccc ttg aca ttc tat ttg gac cct cag tgg caa ctt      1567
Asp Arg Ile Glu Pro Leu Thr Phe Tyr Leu Asp Pro Gln Trp Gln Leu
        455                 460                 465 gca ttg aat ccc tca gaa agg aaa tat tgt gga agt gga ttt cat ggc      1615
Ala Leu Asn Pro Ser Glu Arg Lys Tyr Cys Gly Ser Gly Phe His Gly
    470                 475                 480 tct gac aat gta ttt tca aat atg caa gcc ctc ttt gtt ggc tat gga      1663
Ser Asp Asn Val Phe Ser Asn Met Gln Ala Leu Phe Val Gly Tyr Gly
485                 490                 495                 500 cct gga ttc aag cat ggc att gag gct gac acc ttt gaa aac att gaa      1711
Pro Gly Phe Lys His Gly Ile Glu Ala Asp Thr Phe Glu Asn Ile Glu
                505                 510                 515 gtc tat aac tta atg tgt gat tta ctg aat ttg aca ccg gct cct aat      1759
Val Tyr Asn Leu Met Cys Asp Leu Leu Asn Leu Thr Pro Ala Pro Asn
            520                 525                 530 aac gga act cat gga agt ctt aac cac ctt cta aag aat cct gtt tat      1807
Asn Gly Thr His Gly Ser Leu Asn His Leu Leu Lys Asn Pro Val Tyr
        535                 540                 545 acg cca aag cat ccc aaa gaa gtg cac ccc ctg gta cag tgc ccc ttc      1855
Thr Pro Lys His Pro Lys Glu Val His Pro Leu Val Gln Cys Pro Phe
    550                 555                 560 aca aga aac ccc aga gat aac ctt ggc tgc tca tgt aac cct tcg att      1903
Thr Arg Asn Pro Arg Asp Asn Leu Gly Cys Ser Cys Asn Pro Ser Ile
565                 570                 575                 580 ttg ccg att gag gat ttt caa aca cag ttc aat ctg act gtg gca gaa      1951
Leu Pro Ile Glu Asp Phe Gln Thr Gln Phe Asn Leu Thr Val Ala Glu
                585                 590                 595 gag aag att att aag cat gaa act tta ccc tat gga aga cct aga gtt      1999
Glu Lys Ile Ile Lys His Glu Thr Leu Pro Tyr Gly Arg Pro Arg Val
            600                 605                 610 ctc cag aag gaa aac acc atc tgt ctt ctt tcc cag cac cag ttt atg      2047
Leu Gln Lys Glu Asn Thr Ile Cys Leu Leu Ser Gln His Gln Phe Met
        615                 620                 625 agt gga tac agc caa gac atc tta atg ccc ctt tgg aca tcc tat acc      2095
Ser Gly Tyr Ser Gln Asp Ile Leu Met Pro Leu Trp Thr Ser Tyr Thr
    630                 635                 640 gtg gac aga aat gac agt ttc tct acg gaa gac ttc tcc aac tgt ctg      2143
Val Asp Arg Asn Asp Ser Phe Ser Thr Glu Asp Phe Ser Asn Cys Leu
645                 650                 655                 660 tac cag gac ttt aga att cct ctt agt cct gtc cat aaa tgt tca ttt      2191
Tyr Gln Asp Phe Arg Ile Pro Leu Ser Pro Val His Lys Cys Ser Phe
                665                 670                 675 tat aaa aat aac acc aaa gtg agt tac ggg ttc ctc tcc cca cca caa      2239
Tyr Lys Asn Asn Thr Lys Val Ser Tyr Gly Phe Leu Ser Pro Pro Gln
            680                 685                 690 cta aat aaa aat tca agt gga ata tat tct gaa gct ttg ctt act aca      2287
Leu Asn Lys Asn Ser Ser Gly Ile Tyr Ser Glu Ala Leu Leu Thr Thr
        695                 700                 705 aat ata gtg cca atg tac cag agt ttt caa gtt ata tgg cgc tac ttt      2335
Asn Ile Val Pro Met Tyr Gln Ser Phe Gln Val Ile Trp Arg Tyr Phe
```

```
                    710                 715                 720
cat gac acc cta ctg cga aag tat gct gaa gaa aga aat ggt gtc aat      2383
His Asp Thr Leu Leu Arg Lys Tyr Ala Glu Glu Arg Asn Gly Val Asn
725                 730                 735                 740 gtc gtc agt ggt cct gtg ttt gac ttt gat tat gat gga cgt tgt gat      2431
Val Val Ser Gly Pro Val Phe Asp Phe Asp Tyr Asp Gly Arg Cys Asp
                745                 750                 755 tcc tta gag aat ctg agg caa aaa aga aga gtc atc cgt aac caa gaa      2479
Ser Leu Glu Asn Leu Arg Gln Lys Arg Arg Val Ile Arg Asn Gln Glu
            760                 765                 770 att ttg att cca act cac ttc ttt att gtg cta aca agc tgt aaa gat      2527
Ile Leu Ile Pro Thr His Phe Phe Ile Val Leu Thr Ser Cys Lys Asp
        775                 780                 785 aca tct cag acg cct ttg cac tgt gaa aac cta gac acc tta gct ttc      2575
Thr Ser Gln Thr Pro Leu His Cys Glu Asn Leu Asp Thr Leu Ala Phe
    790                 795                 800 att ttg cct cac agg act gat aac agc gag agc tgt gtg cat ggg aag      2623
Ile Leu Pro His Arg Thr Asp Asn Ser Glu Ser Cys Val His Gly Lys
805                 810                 815                 820 cat gac tcc tca tgg gtt gaa gaa ttg tta atg tta cac aga gca cgg      2671
His Asp Ser Ser Trp Val Glu Glu Leu Leu Met Leu His Arg Ala Arg
                825                 830                 835 atc aca gat gtt gag cac atc act gga ctc agc ttc tat caa caa aga      2719
Ile Thr Asp Val Glu His Ile Thr Gly Leu Ser Phe Tyr Gln Gln Arg
                840                 845                 850 aaa gag cca gtt tca gac att tta aag ttg aaa aca cat ttg cca acc      2767
Lys Glu Pro Val Ser Asp Ile Leu Lys Leu Lys Thr His Leu Pro Thr
            855                 860                 865 ttt agc caa gaa gac tga tatgttttt atccccaaac accatgaatc              2815
Phe Ser Gln Glu Asp
            870 tttttgagag aaccttatat tttatatagt cctctagcta cactattgca ttgttcagaa    2875 actgtcgacc agagttagaa cggagccctc ggtgatgcgg acatctcagg gaaacttgcg    2935 tactcagcac agcagtggag agtgttcctg ttgaatcttg cacatatttg aatgtgtaag    2995 cattgtatac attgatcaag ttcggggaa taaagacaga ccacacctaa aactgccttt     3055 ctgcttctct taaggagaa gtagctgtga acattgtctg gataccagat atttgaatct     3115 ttcttactat tggtaataaa ccttgatggc attgggcaaa cagtagactt atagtagggt    3175 tggggtagcc catgttatgt gactatcttt atgagaattt taaagtggtt ctggatatct    3235 tttaacttgg agtttcattt cttttcattg taatcaaaaa aaaaattaac agaagccaaa    3295 atacttctga gaccttgttt caatctttgc tgtatatccc ctcaaaatcc aagttattaa    3355 tcttatgtgt tttcttttta atttttttgat tggatttctt tagatttaat ggttcaaatg   3415 agttcaactt tgagggacga tctttgaata tacttaccta ttataaaatc ttactttgta    3475 tttgtattta a                                                         3486

<210> SEQ ID NO 2
<211> LENGTH: 873
<212> TYPE: PRT
<213> ORGANISM: H. sapiens

<400> SEQUENCE: 2

Met Asp Val Gly Glu Glu Pro Leu Glu Lys Ala Ala Arg Ala Arg Thr
1               5                   10                  15

Ala Lys Asp Pro Asn Thr Tyr Lys Val Leu Ser Leu Val Leu Ser Val
            20                  25                  30
```

```
Cys Val Leu Thr Thr Ile Leu Gly Cys Ile Phe Gly Leu Lys Pro Ser
         35                  40                  45

Cys Ala Lys Glu Val Lys Ser Cys Lys Gly Arg Cys Phe Glu Arg Thr
         50                  55                  60

Phe Gly Asn Cys Arg Cys Asp Ala Ala Cys Val Glu Leu Gly Asn Cys
 65                  70                  75                  80

Cys Leu Asp Tyr Gln Glu Thr Cys Ile Glu Pro Glu His Ile Trp Thr
                 85                  90                  95

Cys Asn Lys Phe Arg Cys Gly Glu Lys Arg Leu Thr Arg Ser Leu Cys
                100                 105                 110

Ala Cys Ser Asp Asp Cys Lys Asp Lys Gly Asp Cys Cys Ile Asn Tyr
             115                 120                 125

Ser Ser Val Cys Gln Gly Glu Lys Ser Trp Val Glu Pro Cys Glu
         130                 135                 140

Ser Ile Asn Glu Pro Gln Cys Pro Ala Gly Phe Glu Thr Pro Pro Thr
145                 150                 155                 160

Leu Leu Phe Ser Leu Asp Gly Phe Arg Ala Glu Tyr Leu His Thr Trp
                 165                 170                 175

Gly Gly Leu Leu Pro Val Ile Ser Lys Leu Lys Cys Gly Thr Tyr
             180                 185                 190

Thr Lys Asn Met Arg Pro Val Tyr Pro Thr Lys Thr Phe Pro Asn His
         195                 200                 205

Tyr Ser Ile Val Thr Gly Leu Tyr Pro Glu Ser His Gly Ile Ile Asp
         210                 215                 220

Asn Lys Met Tyr Asp Pro Lys Met Asn Ala Ser Phe Ser Leu Lys Ser
225                 230                 235                 240

Lys Glu Lys Phe Asn Pro Glu Trp Tyr Lys Gly Glu Pro Ile Trp Val
                 245                 250                 255

Thr Ala Lys Tyr Gln Gly Leu Lys Ser Gly Thr Phe Phe Trp Pro Gly
             260                 265                 270

Ser Asp Val Glu Ile Asn Gly Ile Phe Pro Asp Ile Tyr Lys Met Tyr
         275                 280                 285

Asn Gly Ser Val Pro Phe Glu Glu Arg Ile Leu Ala Val Leu Gln Trp
290                 295                 300

Leu Gln Leu Pro Lys Asp Glu Arg Pro His Phe Tyr Thr Leu Tyr Leu
305                 310                 315                 320

Glu Glu Pro Asp Ser Ser Gly His Ser Tyr Gly Pro Val Ser Ser Glu
             325                 330                 335

Val Ile Lys Ala Leu Gln Arg Val Asp Gly Met Val Gly Met Leu Met
         340                 345                 350

Asp Gly Leu Lys Glu Leu Asn Leu His Arg Cys Leu Asn Leu Ile Leu
         355                 360                 365

Ile Ser Asp His Gly Met Glu Gln Gly Ser Cys Lys Lys Tyr Ile Tyr
         370                 375                 380

Leu Asn Lys Tyr Leu Gly Asp Val Lys Asn Ile Lys Val Ile Tyr Gly
385                 390                 395                 400

Pro Ala Ala Arg Leu Arg Pro Ser Asp Val Pro Asp Lys Tyr Tyr Ser
                 405                 410                 415

Phe Asn Tyr Glu Gly Ile Ala Arg Asn Leu Ser Cys Arg Glu Pro Asn
                 420                 425                 430

Gln His Phe Lys Pro Tyr Leu Lys His Phe Leu Pro Lys Arg Leu His
             435                 440                 445
```

```
Phe Ala Lys Ser Asp Arg Ile Glu Pro Leu Thr Phe Tyr Leu Asp Pro
    450                 455                 460

Gln Trp Gln Leu Ala Leu Asn Pro Ser Glu Arg Lys Tyr Cys Gly Ser
465                 470                 475                 480

Gly Phe His Gly Ser Asp Asn Val Phe Ser Asn Met Gln Ala Leu Phe
                485                 490                 495

Val Gly Tyr Gly Pro Gly Phe Lys His Gly Ile Glu Ala Asp Thr Phe
            500                 505                 510

Glu Asn Ile Glu Val Tyr Asn Leu Met Cys Asp Leu Leu Asn Leu Thr
        515                 520                 525

Pro Ala Pro Asn Asn Gly Thr His Gly Ser Leu Asn His Leu Leu Lys
    530                 535                 540

Asn Pro Val Tyr Thr Pro Lys His Pro Lys Glu Val His Pro Leu Val
545                 550                 555                 560

Gln Cys Pro Phe Thr Arg Asn Pro Arg Asp Asn Leu Gly Cys Ser Cys
                565                 570                 575

Asn Pro Ser Ile Leu Pro Ile Glu Asp Phe Gln Thr Gln Phe Asn Leu
            580                 585                 590

Thr Val Ala Glu Glu Lys Ile Ile Lys His Glu Thr Leu Pro Tyr Gly
        595                 600                 605

Arg Pro Arg Val Leu Gln Lys Glu Asn Thr Ile Cys Leu Leu Ser Gln
    610                 615                 620

His Gln Phe Met Ser Gly Tyr Ser Gln Asp Ile Leu Met Pro Leu Trp
625                 630                 635                 640

Thr Ser Tyr Thr Val Asp Arg Asn Asp Ser Phe Ser Thr Glu Asp Phe
                645                 650                 655

Ser Asn Cys Leu Tyr Gln Asp Phe Arg Ile Pro Leu Ser Pro Val His
            660                 665                 670

Lys Cys Ser Phe Tyr Lys Asn Asn Thr Lys Val Ser Tyr Gly Phe Leu
        675                 680                 685

Ser Pro Pro Gln Leu Asn Lys Asn Ser Ser Gly Ile Tyr Ser Glu Ala
    690                 695                 700

Leu Leu Thr Thr Asn Ile Val Pro Met Tyr Gln Ser Phe Gln Val Ile
705                 710                 715                 720

Trp Arg Tyr Phe His Asp Thr Leu Leu Arg Lys Tyr Ala Glu Glu Arg
                725                 730                 735

Asn Gly Val Asn Val Val Ser Gly Pro Val Phe Asp Phe Asp Tyr Asp
            740                 745                 750

Gly Arg Cys Asp Ser Leu Glu Asn Leu Arg Gln Lys Arg Arg Val Ile
        755                 760                 765

Arg Asn Gln Glu Ile Leu Ile Pro Thr His Phe Phe Ile Val Leu Thr
    770                 775                 780

Ser Cys Lys Asp Thr Ser Gln Thr Pro Leu His Cys Glu Asn Leu Asp
785                 790                 795                 800

Thr Leu Ala Phe Ile Leu Pro His Arg Thr Asp Asn Ser Glu Ser Cys
                805                 810                 815

Val His Gly Lys His Asp Ser Ser Trp Val Glu Glu Leu Leu Met Leu
            820                 825                 830

His Arg Ala Arg Ile Thr Asp Val Glu His Ile Thr Gly Leu Ser Phe
        835                 840                 845

Tyr Gln Gln Arg Lys Glu Pro Val Ser Asp Ile Leu Lys Leu Lys Thr
    850                 855                 860

His Leu Pro Thr Phe Ser Gln Glu Asp
```

-continued

```
865                 870

<210> SEQ ID NO 3
<211> LENGTH: 3486
<212> TYPE: DNA
<213> ORGANISM: H. sapiens
<220> FEATURE:
<221> NAME/KEY: CDS
<222> LOCATION: (164)...(2785)

<400> SEQUENCE: 3
ggccacgatg gagcgcgacg gctgcgcggg gggcgggagc cgcggcggcg agggcgggcg        60
cgctccccgg gagggcccgg cggggaacgg ccgcgatcgg ggccgcagcc acgctgccga       120
ggcgcccggg gacccgcagg cggccgcgtc cttgctggcc cct atg gac gtg ggg        175
                                                Met Asp Val Gly
                                                 1 gag gag ccg ctg gag aag gcg gcg cgc gcc cgc act gcc aag gac ccc       223
Glu Glu Pro Leu Glu Lys Ala Ala Arg Ala Arg Thr Ala Lys Asp Pro
  5                  10                  15                  20 aac acc tat aaa gta ctc tcg ctg gta ttg tca gta tgt gtg tta aca       271
Asn Thr Tyr Lys Val Leu Ser Leu Val Leu Ser Val Cys Val Leu Thr
             25                  30                  35 aca ata ctt ggt tgt ata ttt ggg ttg aaa cca agc tgt gcc aaa gaa       319
Thr Ile Leu Gly Cys Ile Phe Gly Leu Lys Pro Ser Cys Ala Lys Glu
         40                  45                  50 gtt aaa agt tgc aaa ggt cgc tgt ttc gag aga aca ttt ggg aac tgt       367
Val Lys Ser Cys Lys Gly Arg Cys Phe Glu Arg Thr Phe Gly Asn Cys
     55                  60                  65 cgc tgt gat gct gcc tgt gtt gag ctt gga aac tgc tgt tta gat tac       415
Arg Cys Asp Ala Ala Cys Val Glu Leu Gly Asn Cys Cys Leu Asp Tyr
 70                  75                  80 cag gag acg tgc ata gaa cca gaa cat ata tgg act tgc aac aaa ttc       463
Gln Glu Thr Cys Ile Glu Pro Glu His Ile Trp Thr Cys Asn Lys Phe
 85                  90                  95                 100 agg tgt ggt gag aaa agg ttg acc aga agc ctc tgt gcc tgt tca gat       511
Arg Cys Gly Glu Lys Arg Leu Thr Arg Ser Leu Cys Ala Cys Ser Asp
                105                 110                 115 gac tgc aag gac cag ggc gac tgc tgc atc aac tac agt tct gtg tgt       559
Asp Cys Lys Asp Gln Gly Asp Cys Cys Ile Asn Tyr Ser Ser Val Cys
            120                 125                 130 caa ggt gag aaa agt tgg gta gaa gaa cca tgt gag agc att aat gag       607
Gln Gly Glu Lys Ser Trp Val Glu Glu Pro Cys Glu Ser Ile Asn Glu
        135                 140                 145 cca cag tgc cca gca ggg ttt gaa acg cct cct acc ctc tta ttt tct       655
Pro Gln Cys Pro Ala Gly Phe Glu Thr Pro Pro Thr Leu Leu Phe Ser
    150                 155                 160 ttg gat gga ttc agg gca gaa tat tta cac act tgg ggt gga ctt ctt       703
Leu Asp Gly Phe Arg Ala Glu Tyr Leu His Thr Trp Gly Gly Leu Leu
165                 170                 175                 180 cct gtt att agc aaa cta aaa aaa tgt gga aca tat act aaa aac atg       751
Pro Val Ile Ser Lys Leu Lys Lys Cys Gly Thr Tyr Thr Lys Asn Met
                185                 190                 195 aga ccg gta tat cca aca aaa act ttc ccc aat cac tac agc att gtc       799
Arg Pro Val Tyr Pro Thr Lys Thr Phe Pro Asn His Tyr Ser Ile Val
            200                 205                 210 acc gga ttg tat cca gaa tct cat ggc ata atc gac aat aaa atg tat       847
Thr Gly Leu Tyr Pro Glu Ser His Gly Ile Ile Asp Asn Lys Met Tyr
        215                 220                 225 gat ccc aaa atg aat gct tcc ttt tca ctt aaa agt aaa gag aaa ttt       895
Asp Pro Lys Met Asn Ala Ser Phe Ser Leu Lys Ser Lys Glu Lys Phe
```

```
                230                 235                 240
aat cct gag tgg tac aaa gga gaa cca att tgg gtc aca gct aag tat      943
Asn Pro Glu Trp Tyr Lys Gly Glu Pro Ile Trp Val Thr Ala Lys Tyr
245                 250                 255                 260 caa ggc ctc aag tct ggc aca ttt ttc tgg cca gga tca gat gtg gaa      991
Gln Gly Leu Lys Ser Gly Thr Phe Phe Trp Pro Gly Ser Asp Val Glu
                    265                 270                 275 att aac gga att ttc cca gac atc tat aaa atg tat aat ggt tca gta     1039
Ile Asn Gly Ile Phe Pro Asp Ile Tyr Lys Met Tyr Asn Gly Ser Val
                280                 285                 290 cca ttt gaa gaa agg att tta gct gtt ctt cag tgg cta cag ctt cct     1087
Pro Phe Glu Glu Arg Ile Leu Ala Val Leu Gln Trp Leu Gln Leu Pro
            295                 300                 305 aaa gat gaa aga cca cac ttt tac act ctg tat tta gaa gaa cca gat     1135
Lys Asp Glu Arg Pro His Phe Tyr Thr Leu Tyr Leu Glu Glu Pro Asp
        310                 315                 320 tct tca ggt cat tca tat gga cca gtc agc agt gaa gtc atc aaa gcc     1183
Ser Ser Gly His Ser Tyr Gly Pro Val Ser Ser Glu Val Ile Lys Ala
325                 330                 335                 340 ttg cag agg gtt gat ggt atg gtt ggt atg ctg atg gat ggt ctg aaa     1231
Leu Gln Arg Val Asp Gly Met Val Gly Met Leu Met Asp Gly Leu Lys
                    345                 350                 355 gag ctg aac ttg cac aga tgc ctg aac ctc atc ctt att tca gat cat     1279
Glu Leu Asn Leu His Arg Cys Leu Asn Leu Ile Leu Ile Ser Asp His
                360                 365                 370 ggc atg gaa caa ggc agt tgt aag aaa tac ata tat ctg aat aaa tat     1327
Gly Met Glu Gln Gly Ser Cys Lys Lys Tyr Ile Tyr Leu Asn Lys Tyr
            375                 380                 385 ttg ggg gat gtt aaa aat att aaa gtt atc tat gga cct gca gct cga     1375
Leu Gly Asp Val Lys Asn Ile Lys Val Ile Tyr Gly Pro Ala Ala Arg
390                 395                 400 ttg aga ccc tct gat gtc cca gat aaa tac tat tca ttt aac tat gaa     1423
Leu Arg Pro Ser Asp Val Pro Asp Lys Tyr Tyr Ser Phe Asn Tyr Glu
405                 410                 415                 420 ggc att gcc cga aat ctt tct tgc cgg gaa cca aac cag cac ttc aaa     1471
Gly Ile Ala Arg Asn Leu Ser Cys Arg Glu Pro Asn Gln His Phe Lys
                    425                 430                 435 cct tac ctg aaa cat ttc tta cct aag cgt ttg cac ttt gct aag agt     1519
Pro Tyr Leu Lys His Phe Leu Pro Lys Arg Leu His Phe Ala Lys Ser
                440                 445                 450 gat aga att gag ccc ttg aca ttc tat ttg gac cct cag tgg caa ctt     1567
Asp Arg Ile Glu Pro Leu Thr Phe Tyr Leu Asp Pro Gln Trp Gln Leu
            455                 460                 465 gca ttg aat ccc tca gaa agg aaa tat tgt gga agt gga ttt cat ggc     1615
Ala Leu Asn Pro Ser Glu Arg Lys Tyr Cys Gly Ser Gly Phe His Gly
        470                 475                 480 tct gac aat gta ttt tca aat atg caa gcc ctc ttt gtt ggc tat gga     1663
Ser Asp Asn Val Phe Ser Asn Met Gln Ala Leu Phe Val Gly Tyr Gly
485                 490                 495                 500 cct gga ttc aag cat ggc att gag gct gac acc ttt gaa aac att gaa     1711
Pro Gly Phe Lys His Gly Ile Glu Ala Asp Thr Phe Glu Asn Ile Glu
                    505                 510                 515 gtc tat aac tta atg tgt gat tta ctg aat ttg acg ccg gct cct aat     1759
Val Tyr Asn Leu Met Cys Asp Leu Leu Asn Leu Thr Pro Ala Pro Asn
                520                 525                 530 aac gga act cat gga agt ctt aac cac ctt cta aag aat cct gtt tat     1807
Asn Gly Thr His Gly Ser Leu Asn His Leu Leu Lys Asn Pro Val Tyr
            535                 540                 545 acg cca aag cat ccc aaa gaa gtg cac ccc ctg gta cag tgc ccc ttc     1855
```

```
Thr Pro Lys His Pro Lys Glu Val His Pro Leu Val Gln Cys Pro Phe
    550                 555                 560 aca aga aac ccc aga gat aac ctt ggc tgc tca tgt aac cct tcg att       1903
Thr Arg Asn Pro Arg Asp Asn Leu Gly Cys Ser Cys Asn Pro Ser Ile
565                 570                 575                 580 ttg ccg att gag gat ttt caa aca cag ttc aat ctg act gtg gca gaa       1951
Leu Pro Ile Glu Asp Phe Gln Thr Gln Phe Asn Leu Thr Val Ala Glu
                585                 590                 595 gag aag att att aag cat gaa act tta ccc tat gga aga cct aga gtt       1999
Glu Lys Ile Ile Lys His Glu Thr Leu Pro Tyr Gly Arg Pro Arg Val
                    600                 605                 610 ctc cag aag gaa aac acc atc tgt ctt ctt tcc cag cac cag ttt atg       2047
Leu Gln Lys Glu Asn Thr Ile Cys Leu Leu Ser Gln His Gln Phe Met
                615                 620                 625 agt gga tac agc caa gac atc tta atg ccc ctt tgg aca tcc tat acc       2095
Ser Gly Tyr Ser Gln Asp Ile Leu Met Pro Leu Trp Thr Ser Tyr Thr
    630                 635                 640 gtg gac aga aat gac agt ttc tct acg gaa gac ttc tcc aac tgt ctg       2143
Val Asp Arg Asn Asp Ser Phe Ser Thr Glu Asp Phe Ser Asn Cys Leu
645                 650                 655                 660 tac cag gac ttt aga att cct ctt agt cct gtc cat aaa tgt tca ttt       2191
Tyr Gln Asp Phe Arg Ile Pro Leu Ser Pro Val His Lys Cys Ser Phe
                665                 670                 675 tat aaa aat aac acc aaa gtg agt tac ggg ttc ctc tcc cca cca caa       2239
Tyr Lys Asn Asn Thr Lys Val Ser Tyr Gly Phe Leu Ser Pro Pro Gln
                680                 685                 690 cta aat aaa aat tca agt gga ata tat tct gaa gct ttg ctt act aca       2287
Leu Asn Lys Asn Ser Ser Gly Ile Tyr Ser Glu Ala Leu Leu Thr Thr
                695                 700                 705 aat ata gtg cca atg tac cag agt ttt caa gtt ata tgg cgc tac ttt       2335
Asn Ile Val Pro Met Tyr Gln Ser Phe Gln Val Ile Trp Arg Tyr Phe
    710                 715                 720 cat gac acc cta ctg cga aag tat gct gaa gaa aga aat ggt gtc aat       2383
His Asp Thr Leu Leu Arg Lys Tyr Ala Glu Glu Arg Asn Gly Val Asn
725                 730                 735                 740 gtc gtc agt ggt cct gtg ttt gac ttt gat tat gat gga cgt tgt gat       2431
Val Val Ser Gly Pro Val Phe Asp Phe Asp Tyr Asp Gly Arg Cys Asp
                745                 750                 755 tcc tta gag aat ctg agg caa aaa aga aga gtc atc cgt aac caa gaa       2479
Ser Leu Glu Asn Leu Arg Gln Lys Arg Arg Val Ile Arg Asn Gln Glu
                760                 765                 770 att ttg att cca act cac ttc ttt att gtg cta aca agc tgt aaa gat       2527
Ile Leu Ile Pro Thr His Phe Phe Ile Val Leu Thr Ser Cys Lys Asp
                775                 780                 785 aca tct cag acg cct ttg cac tgt gaa aac cta gac acc tta gct ttc       2575
Thr Ser Gln Thr Pro Leu His Cys Glu Asn Leu Asp Thr Leu Ala Phe
790                 795                 800 att ttg cct cac agg act gat aac agc gag agc tgt gtg cat ggg aag       2623
Ile Leu Pro His Arg Thr Asp Asn Ser Glu Ser Cys Val His Gly Lys
805                 810                 815                 820 cat gac tcc tca tgg gtt gaa gaa ttg tta atg tta cac aga gca cgg       2671
His Asp Ser Ser Trp Val Glu Glu Leu Leu Met Leu His Arg Ala Arg
                825                 830                 835 atc aca gat gtt gag cac atc act gga ctc agc ttc tat caa caa aga       2719
Ile Thr Asp Val Glu His Ile Thr Gly Leu Ser Phe Tyr Gln Gln Arg
                840                 845                 850 aaa gag cca gtt tca gac att tta aag ttg aaa aca cat ttg cca acc       2767
Lys Glu Pro Val Ser Asp Ile Leu Lys Leu Lys Thr His Leu Pro Thr
                855                 860                 865
```

-continued

```
ttt agc caa gaa gac tga tatgtttttt atccccaaac accatgaatc              2815
Phe Ser Gln Glu Asp
    870 tttttgagag aaccttatat tttatatagt cctctagcta cactattgca ttgttcagaa     2875 actgtcgacc agagttagaa cggagccctc ggtgatgcgg acatctcagg gaaacttgcg     2935 tactcagcac agcagtggag agtgttcctg ttgaatcttg cacatatttg aatgtgtaag     2995 cattgtatac attgatcaag ttcgggggaa taaagacaga ccacacctaa aactgccttt     3055 ctgcttctct taaaggagaa gtagctgtga acattgtctg gataccagat atttgaatct     3115 ttcttactat tggtaataaa ccttgatggc attgggcaaa cagtagactt atagtagggt     3175 tggggtagcc catgttatgt gactatcttt atgagaattt taaagtggtt ctggatatct     3235 tttaacttgg agtttcattt cttttcattg taatcaaaaa aaaaattaac agaagccaaa     3295 atacttctga gaccttgttt caatctttgc tgtatatccc ctcaaaatcc aagttattaa     3355 tcttatgtgt tttctttta atttttgat tggatttctt tagatttaat ggttcaaatg       3415 agttcaactt tgagggacga tctttgaata tacttaccta ttataaaatc ttactttgta     3475 tttgtattta a                                                          3486
```

<210> SEQ ID NO 4
<211> LENGTH: 873
<212> TYPE: PRT
<213> ORGANISM: H. sapiens

<400> SEQUENCE: 4

```
Met Asp Val Gly Glu Glu Pro Leu Glu Lys Ala Ala Arg Ala Arg Thr
  1               5                  10                  15

Ala Lys Asp Pro Asn Thr Tyr Lys Val Leu Ser Leu Val Leu Ser Val
             20                  25                  30

Cys Val Leu Thr Thr Ile Leu Gly Cys Ile Phe Gly Leu Lys Pro Ser
         35                  40                  45

Cys Ala Lys Glu Val Lys Ser Cys Lys Gly Arg Cys Phe Glu Arg Thr
     50                  55                  60

Phe Gly Asn Cys Arg Cys Asp Ala Ala Cys Val Glu Leu Gly Asn Cys
 65                  70                  75                  80

Cys Leu Asp Tyr Gln Glu Thr Cys Ile Glu Pro Glu His Ile Trp Thr
                 85                  90                  95

Cys Asn Lys Phe Arg Cys Gly Glu Lys Arg Leu Thr Arg Ser Leu Cys
            100                 105                 110

Ala Cys Ser Asp Asp Cys Lys Asp Gln Gly Asp Cys Cys Ile Asn Tyr
        115                 120                 125

Ser Ser Val Cys Gln Gly Glu Lys Ser Trp Val Glu Glu Pro Cys Glu
    130                 135                 140

Ser Ile Asn Glu Pro Gln Cys Pro Ala Gly Phe Glu Thr Pro Pro Thr
145                 150                 155                 160

Leu Leu Phe Ser Leu Asp Gly Phe Arg Ala Glu Tyr Leu His Thr Trp
                165                 170                 175

Gly Gly Leu Leu Pro Val Ile Ser Lys Leu Lys Cys Gly Thr Tyr Tyr
            180                 185                 190

Thr Lys Asn Met Arg Pro Val Tyr Pro Thr Lys Thr Phe Pro Asn His
        195                 200                 205

Tyr Ser Ile Val Thr Gly Leu Tyr Pro Glu Ser His Gly Ile Ile Asp
    210                 215                 220

Asn Lys Met Tyr Asp Pro Lys Met Asn Ala Ser Phe Ser Leu Lys Ser
```

-continued

```
225                 230                 235                 240
Lys Glu Lys Phe Asn Pro Glu Trp Tyr Lys Gly Glu Pro Ile Trp Val
                245                 250                 255
Thr Ala Lys Tyr Gln Gly Leu Lys Ser Gly Thr Phe Phe Trp Pro Gly
                260                 265                 270
Ser Asp Val Glu Ile Asn Gly Ile Phe Pro Asp Ile Tyr Lys Met Tyr
                275                 280                 285
Asn Gly Ser Val Pro Phe Glu Arg Ile Leu Ala Val Leu Gln Trp
            290                 295                 300
Leu Gln Leu Pro Lys Asp Glu Arg Pro His Phe Tyr Thr Leu Tyr Leu
305                 310                 315                 320
Glu Glu Pro Asp Ser Ser Gly His Ser Tyr Gly Pro Val Ser Ser Glu
                325                 330                 335
Val Ile Lys Ala Leu Gln Arg Val Asp Gly Met Val Gly Met Leu Met
                340                 345                 350
Asp Gly Leu Lys Glu Leu Asn Leu His Arg Cys Leu Asn Leu Ile Leu
                355                 360                 365
Ile Ser Asp His Gly Met Glu Gln Gly Ser Cys Lys Lys Tyr Ile Tyr
                370                 375                 380
Leu Asn Lys Tyr Leu Gly Asp Val Lys Asn Ile Lys Val Ile Tyr Gly
385                 390                 395                 400
Pro Ala Ala Arg Leu Arg Pro Ser Asp Val Pro Asp Lys Tyr Tyr Ser
                405                 410                 415
Phe Asn Tyr Glu Gly Ile Ala Arg Asn Leu Ser Cys Arg Glu Pro Asn
                420                 425                 430
Gln His Phe Lys Pro Tyr Leu Lys His Phe Leu Pro Lys Arg Leu His
                435                 440                 445
Phe Ala Lys Ser Asp Arg Ile Glu Pro Leu Thr Phe Tyr Leu Asp Pro
                450                 455                 460
Gln Trp Gln Leu Ala Leu Asn Pro Ser Glu Arg Lys Tyr Cys Gly Ser
465                 470                 475                 480
Gly Phe His Gly Ser Asp Asn Val Phe Ser Asn Met Gln Ala Leu Phe
                485                 490                 495
Val Gly Tyr Gly Pro Gly Phe Lys His Gly Ile Glu Ala Asp Thr Phe
                500                 505                 510
Glu Asn Ile Glu Val Tyr Asn Leu Met Cys Asp Leu Leu Asn Leu Thr
                515                 520                 525
Pro Ala Pro Asn Asn Gly Thr His Gly Ser Leu Asn His Leu Leu Lys
                530                 535                 540
Asn Pro Val Tyr Thr Pro Lys His Pro Lys Glu Val His Pro Leu Val
545                 550                 555                 560
Gln Cys Pro Phe Thr Arg Asn Pro Arg Asp Asn Leu Gly Cys Ser Cys
                565                 570                 575
Asn Pro Ser Ile Leu Pro Ile Glu Asp Phe Gln Thr Gln Phe Asn Leu
                580                 585                 590
Thr Val Ala Glu Glu Lys Ile Ile Lys His Glu Thr Leu Pro Tyr Gly
                595                 600                 605
Arg Pro Arg Val Leu Gln Lys Glu Asn Thr Ile Cys Leu Leu Ser Gln
                610                 615                 620
His Gln Phe Met Ser Gly Tyr Ser Gln Asp Ile Leu Met Pro Leu Trp
625                 630                 635                 640
Thr Ser Tyr Thr Val Asp Arg Asn Asp Ser Phe Ser Thr Glu Asp Phe
                645                 650                 655
```

```
Ser Asn Cys Leu Tyr Gln Asp Phe Arg Ile Pro Leu Ser Pro Val His
            660                 665                 670

Lys Cys Ser Phe Tyr Lys Asn Asn Thr Lys Val Ser Tyr Gly Phe Leu
            675                 680                 685

Ser Pro Pro Gln Leu Asn Lys Asn Ser Ser Gly Ile Tyr Ser Glu Ala
            690                 695                 700

Leu Leu Thr Thr Asn Ile Val Pro Met Tyr Gln Ser Phe Gln Val Ile
705                 710                 715                 720

Trp Arg Tyr Phe His Asp Thr Leu Leu Arg Lys Tyr Ala Glu Glu Arg
                    725                 730                 735

Asn Gly Val Asn Val Val Ser Gly Pro Val Phe Asp Phe Asp Tyr Asp
                740                 745                 750

Gly Arg Cys Asp Ser Leu Glu Asn Leu Arg Gln Lys Arg Arg Val Ile
            755                 760                 765

Arg Asn Gln Glu Ile Leu Ile Pro Thr His Phe Phe Ile Val Leu Thr
            770                 775                 780

Ser Cys Lys Asp Thr Ser Gln Thr Pro Leu His Cys Glu Asn Leu Asp
785                 790                 795                 800

Thr Leu Ala Phe Ile Leu Pro His Arg Thr Asp Asn Ser Glu Ser Cys
                    805                 810                 815

Val His Gly Lys His Asp Ser Ser Trp Val Glu Glu Leu Leu Met Leu
                820                 825                 830

His Arg Ala Arg Ile Thr Asp Val Glu His Ile Thr Gly Leu Ser Phe
            835                 840                 845

Tyr Gln Gln Arg Lys Glu Pro Val Ser Asp Ile Leu Lys Leu Lys Thr
            850                 855                 860

His Leu Pro Thr Phe Ser Gln Glu Asp
865                 870

<210> SEQ ID NO 5
<211> LENGTH: 646
<212> TYPE: DNA
<213> ORGANISM: H. sapiens
<220> FEATURE:
<221> NAME/KEY: promoter
<222> LOCATION: (0)...(0)
<223> OTHER INFORMATION: PC-1 promoter sequence
<220> FEATURE:
<221> NAME/KEY: misc_feature
<222> LOCATION: (1)...(646)
<223> OTHER INFORMATION: n = A,T,C or G

<400> SEQUENCE: 5
aaaccaacgt agngacgtgg gaatcgaaat atccttaggt gtgttcagta tatgtgaacc      60
cacgtatttt aagtggacga tttctctctc agagtaccgt aggtagtggg ggacggggcg     120
cagaggggga gaaacagaaa gtcgccttcc tccatggttc atttgcattt ccatccagaa     180
actcacaggt cgaccccaag actccactct ctcccgcctt tgagaagccg gaccggcatc     240
ggcggctgca tccttctcct cctccccgct ctattttggg gccccatgat ctcatgcctt     300
ctgcagacca cacgctgcaa ttccagccca gcccgcgccg cgaggccacg cagggcgatt     360
cctgcaagtg tcgggagggt ggccggggcg cgggagggg acgcttggg gggaagttta      420 agacacgccc acgtaaggga cccaaaataa ccgacacaca gagtgcccga aatcagacag     480
gaagccaaat aatccggggc gttgagtcgc tttgccctga ctgcgagagc cggtgtagg      540 gcggggagcc aaggatctga ccgcgagggg cgggcgcggc ggggaggggc ggggcgggc      600
```

```
                                        -continued
gggcggcgcg gggcctatta aaggcgcggc ggggcagcgg ggccgg            646
```

<210> SEQ ID NO 6
<211> LENGTH: 350
<212> TYPE: DNA
<213> ORGANISM: H. sapiens
<220> FEATURE:
<221> NAME/KEY: 3'UTR
<222> LOCATION: (0)...(0)
<223> OTHER INFORMATION: allele "A"

<400> SEQUENCE: 6

```
agccaagaag actgatatgt tttttatccc caaacaccat gaatctttt gagagaacct    60
tatatttat atagtcctct agctacacta ttgcattgtt cagaaactgt cgaccagagt   120
tagaacggag ccctcggtga tgcggacatc tcagggaaac ttgcgtactc agcacagcag   180
tggagagtgt tcctgttgaa tcttgcacat atttgaatgt gtaagcattg tatacattga   240
tcaagttcgg gggaataaag acagaccaca cctaaaactg cctttctgct tctcttaaag   300
gagaagtagc tgtgaacatt gtctggatac cagatatttg aatctttctt               350
```

<210> SEQ ID NO 7
<211> LENGTH: 350
<212> TYPE: DNA
<213> ORGANISM: H. sapiens
<220> FEATURE:
<221> NAME/KEY: 3'UTR
<222> LOCATION: (0)...(0)
<223> OTHER INFORMATION: allele "P"

<400> SEQUENCE: 7

```
agccaagaag actgatatgt tttttatccc caaacaccat gaatctttt gagagaacct    60
tatatttat atagtcctct agctacacta ttgcattgtt cagaaactgt cgaccagagt   120
tagaacagag ccctccgtga tgcggacatc tcagggaaac ttgcgtactc agcacagtag   180
tggagagtgt tcctgttgaa tcttgcacat atttgaatgt gtaagcattg tatacattga   240
tcaagttcgg gggaataaag acagaccaca cctaaaactg cctttctgct tctcttaaag   300
gagaagtagc tgtgaacatt gtctggatac cagatatttg aatctttctt               350
```

<210> SEQ ID NO 8
<211> LENGTH: 350
<212> TYPE: DNA
<213> ORGANISM: H. sapiens
<220> FEATURE:
<221> NAME/KEY: 3'UTR
<222> LOCATION: (0)...(0)
<223> OTHER INFORMATION: allele "N"

<400> SEQUENCE: 8

```
agccaagaag actgatatgt tttttatccc caaacaccat gaatctttt gagagaacct    60
tatatttat atagtcctct agctacacta ttgcattgtt cagaaactgt cgaccagagt   120
tagaacagag ccctcggtga tgcggacatc tcagggaaac ttgcgtactc agcacagtag   180
tggagagtgt tcctgttgaa tcttgcacat atttgaatgt gtaagcattg tatacattga   240
tcaagttcgg gggaataaag acagaccaca cctaaaactg cctttctgct tctcttaaag   300
gagaagtagc tgtgaacatt gtctggatac cagatatttg aatctttctt               350
```

<210> SEQ ID NO 9
<211> LENGTH: 23
<212> TYPE: DNA
<213> ORGANISM: H. sapiens

<400> SEQUENCE: 9
ctgtgttcac tttggacatg ttg                                                   23

<210> SEQ ID NO 10
<211> LENGTH: 22
<212> TYPE: DNA
<213> ORGANISM: H. sapiens

<400> SEQUENCE: 10
gacgttggaa gataccaggt tg                                                    22

<210> SEQ ID NO 11
<211> LENGTH: 109
<212> TYPE: DNA
<213> ORGANISM: H. sapiens
<220> FEATURE:
<221> NAME/KEY: misc_feature
<222> LOCATION: (1)...(109)
<223> OTHER INFORMATION: n = A,T,C or G

<400> SEQUENCE: 11
ctctcgctgg taggtccgcg gccaggcccc ggcgcccggg agggctggga atacngggag            60
ggcggcgccg agctcctgcg ctctcagcgc actcagcacc gggcacgga                      109

<210> SEQ ID NO 12
<211> LENGTH: 279
<212> TYPE: DNA
<213> ORGANISM: H. sapiens

<400> SEQUENCE: 12
tgagctccac cgggccggcg gccgctctag aactagtgga tcatgccact gtaccctagc           60
ctgggtaaca gagtaagaca ctatctctaa aaataaaaaa taagataaaa tattttttaa          120 aaagaaacc atgtaatttt ctcttttctc cctacaggta ttgagaaggt aattaggtgt           180
gtgtgtgtgt gtgtgtgtgt gtgtgtgtgt gtatgtgtgt gcacagcctt attaagaatg          240
tgattgaggt aaacattatc tcctattccc aagggtac                                  279

<210> SEQ ID NO 13
<211> LENGTH: 243
<212> TYPE: DNA
<213> ORGANISM: H. sapiens

<400> SEQUENCE: 13 agattttgc cttactttat taccccatct gtattttcta aagtagtatt tgaacctagt           60
gtacacctaa cttagttgta ttcgttgatg tttactttga attatataat gattagaaac          120
atctgactta tcgttcaatt ttttcagtta accaggtaag gatgagcagg gaaaaaagtg          180
gagttatggt cattaggaaa agatccacta gttctagagc ggccgccacg cccggtggag          240
ctt                                                                        243

<210> SEQ ID NO 14
<211> LENGTH: 231
<212> TYPE: DNA
<213> ORGANISM: H. sapiens
<220> FEATURE:
<221> NAME/KEY: misc_feature
<222> LOCATION: (1)...(231)
<223> OTHER INFORMATION: n = A,T,C or G

<400> SEQUENCE: 14

```
cgcggcggcc gttctagaac tagtggatca tactcacgaa gacagcaatt ctgtgttcac      60
tttggacatg ttgaatttga gacataaaac acattttgct gatgtttgtt tctagaacat     120
agtcaaggtc aggtgctcgt tgggctctgc agcaacctgg tatcttccaa cctcttaacg     180
gggctntaca taagtgttat cttttatatt aagantcatg gctattgggc c              231
```

<210> SEQ ID NO 15
<211> LENGTH: 313
<212> TYPE: DNA
<213> ORGANISM: H. sapiens

<400> SEQUENCE: 15

```
aatctgttca catactttgt ttgtggaatc tgtcttaatg tgtctcacaa gcatcacaat      60
tattattact gttaagtgtg ttcattttat tttcttgaaa atattttagg tgagaagcag     120
ggtaagatta tattctgagg tattaatttt tctttttta gaagtacagc atcattttt      180 tctttccaaa ttaagatgat aaaaataata aaatcactgg tttattaaac attacaggtt     240
gagtatcctt tatccaaaat gtttggtatg agaactgttt tggattttgg actttttgg      300 attttgcaat att                                                          313
```

<210> SEQ ID NO 16
<211> LENGTH: 313
<212> TYPE: DNA
<213> ORGANISM: H. sapiens

<400> SEQUENCE: 16

```
ccgcagcccg ggggatcaca cagaccttag tggaaaatct tcactggacc tgtgccaaga      60 aggggggtaca tcttcattgg atatgtcttg tctttgcttc tttaaacatt tttttttctt    120
tttcattacc caggtttgaa actaagtgag taacttcaga gtttactgct ggaatatcac     180
catttcagtg agattgacta ggcaggcagt cttcttggaa aaagtactgg cagaacctaa     240
ctgtttcact aaacttttct aatgggcaaa gtagttgaac cttgtgtagg gcgccttatc     300
tttaataatg tga                                                          313
```

<210> SEQ ID NO 17
<211> LENGTH: 382
<212> TYPE: DNA
<213> ORGANISM: H. sapiens

<400> SEQUENCE: 17

```
taagagaaaa atgaagtcat ctttaagatt ggatttgtat ccacagtgtt gctttataat      60
tcatcctgaa ttttatctg attaaaatcc tccctgggta atttttttta cgtgatttag      120
actgctgtgg taccactgct aaatgaggta agccaattgt cagatgtatt taataacaat     180 gtttatttt ttcccttcta gaaaaatgtt caccgtaagc tctgcatttc aacttctatc      240
tgtttgaaga agtgagatgg gattgtaaca ttttttgagg gaatagattt aagataaaag     300
aaaaacaact tattttccaa taggtagtta agtaaggaaa cccaggttct gatctttgct     360
ctgccacaaa ctagctgtgg ct                                               382
```

<210> SEQ ID NO 18
<211> LENGTH: 312
<212> TYPE: DNA
<213> ORGANISM: H. sapiens

<400> SEQUENCE: 18

```
actacataaa atcttaagag gttgcgtttt gccattacct gattttttg tttttctttc       60
```

```
cttaaactta ttataattcc atgtagcttc agttatcggt ttcttttttga tgattttttt    120 ctgtgaatgt atttaacatt aagtaaacac aacttgcata taatctgttt tatcttttt    180 agggattaac cagtgagttc tttgtttttc tactaaaata gttaattatt ctcatctatt    240
tcaatcagag taaaataacc agattctcta gagcttttaa taactgattt catttagtgt    300
gtctgtggcc at                                                       312

<210> SEQ ID NO 19
<211> LENGTH: 382
<212> TYPE: DNA
<213> ORGANISM: H. sapiens

<400> SEQUENCE: 19
taatctctga ctatttaata tgttgttgct gcttaagagt catattacat gattattgtc    60
gtctaagtgc tgaagcttgt tgaccttaaa agcattctag cactagagag gaatgcattg    120
gtgtggtatg aaaacatact ttcctaagag atgaatgttg catgatttct taatttttcct   180 tcattttctg ctccagattt ggaatgggta tgtgaaatga attttttcta ggatctgtaa    240
tatagaacag cttattctta tgtaatctcc tttttattga atcctgagct ttagcatttg    300
agtgatatgt tggctgaaaa atgagaactg aagaactctt tctcaaagag tttagataga    360
tggtaaatgg acagtaaaac ta                                            382

<210> SEQ ID NO 20
<211> LENGTH: 307
<212> TYPE: DNA
<213> ORGANISM: H. sapiens

<400> SEQUENCE: 20
gggaaaataa agttttcaaa taaaaccctt gatttcaaac acaatagatg cgaaatagca    60
tttactagct cttaatgaca ttttcaatga aaaaaactat attttacacc caaacaattg    120
tcagccatct tttattttg tttgttcttc attttagttc agtaagatga aggtctgta    180 ggcaattaat ttctattgta aatacttcgt tttgtagaaa tgatatacta ttttccccta    240
gactacaaca aaactttgct atttgctatg atgttttata tcgaaataaa ttctttagta    300
aatgatc                                                             307

<210> SEQ ID NO 21
<211> LENGTH: 329
<212> TYPE: DNA
<213> ORGANISM: H. sapiens

<400> SEQUENCE: 21
gaatttcaaa gctgtaaatt atttctcagt agaactgtta caccagtgtt ataaaattta    60
atccctatca attgaggaat tattttttcc attctgtttt tcaatgtgtt cgtaaaatat    120
tacattttga tactgtttga tttagaccac acagtgagta agtacatttt tctcagtaat    180
tatttcatta aacccagtca tcaaactgaa cctcgctttg aaggaggctg ctagaccatt    240
ttataagatt ctatcatttc tggaaaaagc aagtattata cacaatatta ctaaatataa    300
ggatgcactt taaacaaaat aagagttgg                                     329

<210> SEQ ID NO 22
<211> LENGTH: 381
<212> TYPE: DNA
<213> ORGANISM: H. sapiens
```

-continued

<400> SEQUENCE: 22

| gtcttagttt aatgtgaatc agctcattgt agttgcatcc actggcccaa atctatcaat | 60 |
|---|---|
| ctgtcggtct ttcttcttt ctttgtttct ttcttttttt tttttttaa cagagatagc | 120 |
| tttatgtata aatagccatt agtgtggaag gtatcacatg aggttgtgct tcccattctt | 180 |
| aggtcatcat catggtaatc tgaatttgca ttatttactc ttcaggataa agggctgaag | 240 |
| aaagtttact tgatggtttc ccaatttttt ctgaatgttg tagttaattc tttttaaaa | 300 |
| atgtagtttc ttatggacag tctttaggaa aaaatacat taaatataaa atataagtga | 360 |
| aacacagaat tcacagaaac c | 381 |

<210> SEQ ID NO 23
<211> LENGTH: 382
<212> TYPE: DNA
<213> ORGANISM: H. sapiens

<400> SEQUENCE: 23

| gattttgaaa aaagtgaagt gataggtaca gctgaaattc tgtcttacct atcagatctt | 60 |
|---|---|
| caactaatat gagtgctaca cccatgttta acgaatttaa ccttggaagt gaaagaagtt | 120 |
| ctgctctgca tattaaattt tttgttaaag ttacagcatg ttttgggatt tttttttct | 180 |
| cctaggcatg gtactattca tgtaagtata tctctgtgat aactttgaat atggtcatat | 240 |
| taagaatacc ttcctttagg ccgggcacag tggctcatgc ctgtaatcgc agcactttgg | 300 |
| gaggccaaag tgggtggtca cctgaggtca ggagttcgag accagcctgg ccaacatggt | 360 |
| gaaacccta aaatacatat ac | 382 |

<210> SEQ ID NO 24
<211> LENGTH: 361
<212> TYPE: DNA
<213> ORGANISM: H. sapiens

<400> SEQUENCE: 24

| gatccaaact ctgcatttaa ataccaaggc aggttttaaa gagttcattt aagtcattac | 60 |
|---|---|
| attgtagcca ctgaaaggaa ttagacagac ctttagggat ctgacattct atattttgt | 120 |
| attatgtttt aattatagta tacaatcaac tattaattct tatgtttgtt ccctccagt | 180 |
| taactatgaa ggcattgccc gaaatctttc tgtgagtatc tttattttcc attatctagt | 240 |
| tattttact tttgtataat atatattgag agaaaagttt cagcatctat tattgggatt | 300 |
| gaaggattag aatattttag taatctgggc caacatggaa atgctgtgta gtttaaagat | 360 |
| c | 361 |

<210> SEQ ID NO 25
<211> LENGTH: 384
<212> TYPE: DNA
<213> ORGANISM: H. sapiens

<400> SEQUENCE: 25

| ctgatgaaat gtttgtgaaa aaaaatttca tatgaagtta gaaagcaatt tcaagaaaag | 60 |
|---|---|
| ttgcactttt ttatagatat tagggaaata tctttcccta ataaatatct ttccctaaaa | 120 |
| aagttgacac tttttagat attagggaaa taatagtttt tctttgctgt ttgcaatttc | 180 |
| agtgccgggg cattgtaagt tctgacagtc tcccaggtaa acttagtctg atcggttagt | 240 |
| gattcagggt aaccattggg ccctttctaa caatattgtt atgtgaaaac tgtataagta | 300 |
| tgattctctt cactctaacc caggattct aatgtcggcc tatggatgtt tgagttagat | 360 | aattctttgt tgtggagagc tgtc					384

<210> SEQ ID NO 26
<211> LENGTH: 381
<212> TYPE: DNA
<213> ORGANISM: H. sapiens

<400> SEQUENCE: 26
aaaagataga ggtgacttct taatgctttt caaagccagg tggttttatt taccgttgtg			60 ttggtttaac aaaatagtta catactttt aatcaatgaa ataatgtta tgattatcaa			120 ttatgtttta tgaaaggact ttacattttt aattcatata tgtcaacatt aggaatgcaa			180 gtgagtaaac ctattatact taattggatt aaatctaaag aaaaaatgat atgcaaagtt			240 ttagacttga aaacatactg tgattatatg tcttgaatga gaattaatgg aacatacttt			300 cataaagcta ttttcttg aacattaaag aatttgtta agttttata ttcattggct			360 attactaaaa agtcaaaaaa c						381

<210> SEQ ID NO 27
<211> LENGTH: 383
<212> TYPE: DNA
<213> ORGANISM: H. sapiens

<400> SEQUENCE: 27
aaaactaaga gacctatcct agatgtcctt agattatgtg tgtgataggg ttaaaactat			60 atttcccaca aagtccactg agcgtggtag ttttcctctt atcttatcat aaccagtttg			120 tatatgtaca atgtggataa cagaattttt gggaccaact tgtagacagc tgaaatgcac			180 tgataaactt cctttctgg ccatctaggc cctgtgtggt aagtgtgaac aggtgccttt			240 tttcccttct gaaatagac ctgaaatagg attatcaaaa gcaggtcaca ttgtaggcaa			300 cttttgtggag atgatggtga ggcaagacag attttttacct tcttcctgac tctcagactc			360 actgaagaaa tgtggggaac atg					383

<210> SEQ ID NO 28
<211> LENGTH: 384
<212> TYPE: DNA
<213> ORGANISM: H. sapiens

<400> SEQUENCE: 28
catatcagta tttctattaa aaataaccta gtcttaaata ctctaaaacc caagagagtt			60 ttatactttt attttagtta aagagtaaat gactcatgta tttggtttta aaaagtaaa			120 gatcatggca caagtctact atttgtttga tttgaaacat ctaagtaact ctaccatctt			180 gaaattatgc agatttactt cggtaagtat cgtcaagaag tttggtccag tatgtatggt			240 ttgatagcac cctctgcata gcatgtgctg taaaaatact taataatcaa attagaattt			300 aggagtgggg gtaggtaaac atatgtttta attctagggg gcgcatgtaa atcttttgtg			360 atatatcttt tctctttcta gttt					384

<210> SEQ ID NO 29
<211> LENGTH: 339
<212> TYPE: DNA
<213> ORGANISM: H. sapiens

<400> SEQUENCE: 29
gtgaaagagc aacactcttg ccttgaaaga gaaaaaaaaa tccactaata caagactatc			60

| ataaatgatc tttgttctat gttggaataa tcaatctata gcggtctatg ttacaaaatt | 120 |
| taaaacatgt ctctcagtcc ttacaaatag ttttataacc ttttttcaga ttttgccgaa | 180 |
| ggtaaggcat gctacacact caagctcgga atgtgaagca ggcattttct catcagtgtg | 240 |
| aaatgcagag aactggcttg ggggtattat ttgagaataa ccaataaaat aaagggagtt | 300 |
| ctggaggacc acctgatgaa acatagaggt ttctttgct | 339 |

<210> SEQ ID NO 30
<211> LENGTH: 327
<212> TYPE: DNA
<213> ORGANISM: H. sapiens

<400> SEQUENCE: 30

| gtcttcttaa ttgtttatgc ttgtaccctt tgtaatcagt ttttttaata gttaaaagta | 60 |
| aatcttcaat ataattaagt agaggaaagg attagatgag tgtatcacac tatatattat | 120 |
| catataatgc acactaacta catttatttt catcctgtga cccaagagaa gattagacag | 180 |
| aaatgcaagt atttgtcacc tctttatgtg tggccatttc aaattaatga ttaagcagaa | 240 |
| cattaaatgc atagtttctc actgttcacc ttggctttat actcagttcc cgcattagag | 300 |
| gaacactgaa gagggagtca gaaaaat | 327 |

<210> SEQ ID NO 31
<211> LENGTH: 427
<212> TYPE: DNA
<213> ORGANISM: H. sapiens

<400> SEQUENCE: 31

| tttaatattg taaagcattt ttacactta gttagaaaaa aagatgaata tactagtagg | 60 |
| aaaataggga aggacatgag ctgacagcta gagcttcata attttatgat gtagttcacc | 120 |
| tttaaatatt aataaagcaa ttttcttctc tgtgcctgat atctgagagt tcttctcatt | 180 |
| ttcgttcttc aggacaccac cacgtaagtt ttttcctctc ctgaccttcc cttttctcct | 240 |
| ttttgttttc tttcttgttt ataaatccta ccatacatta tagggtaata tatatattac | 300 |
| ctattatata tatataaat attacctatt ttatatatat attatatata taatatatat | 360 |
| aaagtatata tattactatt ttatatatat atagctatat atatataccct ttgtttattt | 420 |
| attgtga | 427 |

<210> SEQ ID NO 32
<211> LENGTH: 380
<212> TYPE: DNA
<213> ORGANISM: H. sapiens

<400> SEQUENCE: 32

| ctcatcttga aaagacttct taaatatttt attttttgtaa aggacttgac caaacacata | 60 |
| acattttccc tcgaccctgt acttgggaaa gttttacagg tttaagatgg tactcagcta | 120 |
| attttttaaaa atgctcccct aaccatgaga agtataatt tcctatgtta tttgtgaaga | 180 |
| atgaaaaagt tgtcctcttt tctctttgta gaactattca aggtaaataa tgttaactct | 240 |
| atatttgata attttaatga atttgtgcac ataggcat aattcatatg tataggactt | 300 |
| atggtctaaa ttaaatgaat taataccaaa tacattctta aaggtttaac tttgagaata | 360 |
| ctagtacaca aaaattctac | 380 |

<210> SEQ ID NO 33
<211> LENGTH: 384

```
<210> SEQ ID NO 33
<211> LENGTH: 384
<212> TYPE: DNA
<213> ORGANISM: H. sapiens

<400> SEQUENCE: 33
ctgggtgata tagcacgact ctgtctctaa acaaaaaaca aaacaaaacg aagactgaag      60
ccaaacttga ctttatcttt atttactata aatgctaatt ttgaatcatg gtgttaattt     120
atttcacacg tcaacatggt cccttgttct tttgaaacta cactggcttc tatcttgttt     180
cagttataga ggcagtaaga acatatttca ttactcttaa aaataggaat taccatccag     240
tagaaatggg attaccatcc agttgagtca acagaacctt ttttatccag tgtcgtatgt     300
ttatgtgtat gacacttctg actacacagg aagcctcttg aaatatctga ttaattttga     360
tgttttgctc aatgttcagt aaaa                                            384

<210> SEQ ID NO 34
<211> LENGTH: 328
<212> TYPE: DNA
<213> ORGANISM: H. sapiens

<400> SEQUENCE: 34
gttcttatat ttaattattg gttggaattt gattttata tgtattaaaa gcatgctcta       60
ctgaaatatt catcaaaagg aagatagtta tttctttctt aaaatgaata ttggcatgtt     120
ttacagaaaa atgtgtggta agtagctttt gtatatttac tttgcatgtt gaaaatctag     180
acatatgcat atttgtttat gtcacccatc tgacattaca gtgagagaaa gcacaactga     240
gtacacatgg acttcgaaat tataggatgc ttttaaattt gatcttttaa gatgacatat     300
ctttggggaa gactaccctg tctgcttt                                        328

<210> SEQ ID NO 35
<211> LENGTH: 384
<212> TYPE: DNA
<213> ORGANISM: H. sapiens

<400> SEQUENCE: 35
aattaaacaa acatgcatgg tatgtattag aaggaaagct actcaagagg agagatgatg      60
cctaacaaat catgtggcac gttccacttc agagctgaaa tctcgtaaat gattaaactg     120
gggagatgga gcacttatag aagtgaactg agtgttctct tggtaacttt tcttttatat     180
ttcctattct cctagcatgg atttaaaaaa gaaaaatatt cctatcctgc tcactggtaa     240
ttaacatagg tttaaaatgg cttcaaatgt ggccctatag acggttaaaa ttgtacctta     300
tcttggcaaa acttcagagc accagtcagt gcatgcaagg tgccattttt tattgagatg     360
cttagaatgt ttctttctgt gcac                                            384
```

POLYMORPHIC HUMAN PC-1 SEQUENCES ASSOCIATED WITH INSULIN RESISTANCE

CROSS-REFERENCE

This application claims priority to provisional patent application No. 60/108,853, filed Nov. 18, 1998.

Insulin resistance occurs in 25% of non-diabetic, non-obese, apparently healthy individuals, and predisposes them to both diabetes and coronary artery disease. Diabetes mellitus is a major health problem in the United States affecting approximately 7% of the population. The most common form of diabetes mellitus is non-insulin-dependent diabetes mellitus (NIDDM or type II diabetes). Hyperglycemia in type II diabetes is the result of both resistance to insulin in muscle and other key insulin target tissues, and decreased beta cell insulin secretion. Longitudinal studies of individuals with a strong family history of diabetes indicate that the insulin resistance precedes the secretory abnormalities. Prior to developing diabetes these individuals compensate for their insulin resistance by secreting extra insulin. Diabetes results when the compensatory hyperinsulinemia fails. The secretory deficiency of pancreatic beta cells then plays a major role in the severity of the diabetes.

Reaven (1988) *Diabetes* 37:1595–607 were the first to have investigated insulin resistant, non-diabetic, healthy individuals from the general population who are non-obese. Strikingly, they observed that 25% of them have insulin resistance that is of a similar magnitude to that seen in type II diabetes patients. These individuals compensate by having insulin levels that are 3–4 times higher than normal. These elevated insulin levels are sufficient to maintain normoglycemia. Others have also confirmed that a large proportion of the non-diabetic population is insulin resistant. These insulin resistant, non-diabetic individuals have a much higher risk for developing type II diabetes than insulin sensitive subjects.

However, even without developing hyperglycemia and diabetes, these insulin resistant individuals pay a significant price in terms of general health. Insulin resistance results in an increased risk for having elevated plasma triglycerides (TG), lower high density lipoproteins (HDL), and high blood pressure, a cluster of abnormalities that have been termed by different investigators as either Syndrome X, the insulin resistance syndrome, or the metabolic syndrome. It is believed that either the hyperinsulinemia, insulin resistance, or both play a direct role in causing these abnormalities. Data from ethnic, family, and longitudinal studies suggest that a major component of resistance is inherited.

The cellular response to insulin is mediated through the insulin receptor (IR), which is a tetrameric protein consisting of two identical extracellular alpha subunits that bind the hormone and two identical transmembrane beta subunits that have intracellular tyrosine kinase activity. When insulin binds to the IR alpha subunit, the beta subunit tyrosine kinase domain is activated, and insulin action ensues. When insulin activates the receptor, the beta subunit is autophosphorylated at the juxtamembrane domain, the tyrosine kinase domain and the C-terminal domain. Subsequently, endogenous substrates including IRS-1, IRS-2 and SHC are tyrosine phosphorylated. These phosphorylated substrates act as docking molecules to activate SH2 domain molecules including: GRB-2 which activates the ras pathway; the p85 subunit of PI-3-kinase; protein tyrosine phosphatase PTP2/SYP; PLCγ/NCK; AKT and others.

PC-1 is a class II transmembrane glycoprotein that is located both on plasma membranes and in the endoplasmic reticulum. PC-1 is the same protein as liver nucleotide pyrophosphatase/alkaline phosphodiesterase I. In addition to muscle tissue, PC-1 has been reported to be expressed in plasma and intracellular membranes of plasma cells, placenta, the distal convoluted tubule of the kidney, ducts of the salivary gland, epididymis, proximal part of the vas deferens, chondrocytes and dermal fibroblasts. PC-1 exists as a disulfide linked homodimer of 230–260 kDa; the reduced form of the protein has a molecular size of 115–135 kDa, depending on the cell type. Human PC-1 is predicted to have 873 amino acids.

PC-1 is inserted into the plasma membrane such that there is a small cytoplasmic amino terminus, and a larger extracellular carboxyl terminus. The extracellular domain of PC-1 has a high cysteine region that is involved in dimer formation, an ATP binding site and enzymatic activity which cleaves sugar-phosphate, phosphosulfate, pyrophosphate, and phosphodiesterase linkages. The active enzyme site for phosphodiesterase and pyrophosphatase contains a key threonine residue, however a mutation of this residue does not impair the ability of PC-1 to inhibit IR function.

Belli et al. (1993) *Eur J Biochem* 217(1):421–8 discloses the existence of enzymatically active water-soluble forms of PC-1. Biosynthetic studies revealed a single, monomeric, endoglycosidase-H-sensitive membrane PC-1 precursor, which was gradually converted to a disulphide-bonded, endoglycosidase-H-resistant form. The soluble form of PC-1 does not appear to arise by proteolytic cleavage from the cell surface, although cleavage inside the cell remains a possibility. The data suggest that the most likely site of cleavage is between Pro 152 and Ala 153.

PC-1 levels are increased in fibroblasts from most patients with typical NIDDM and insulin resistance. In addition, overexpression of PC-1 in transfected cultured cells reduces insulin-stimulated tyrosine kinase activity (Goldfine et al. (1998) *Mol Cell Biochem* 182:177–184). PC-1 content in fibroblasts negatively correlates with both decreased in vivo insulin sensitivity and decreased in vitro IR autophosphorylation (Frittitta et al. (1998) *Diabetes* 47:1095–1100).

In cells from insulin-resistant subjects, insulin stimulation of glycogen synthetase was decreased. PC-1 content is also elevated in fibroblats, muscle and fat of non-diabetic insulin resistant subjects. The elevation of PC-1 content may be a primary factor in the cause of insulin resistance, although the mechanism by which PC-1 inhibits insulin receptor activity is unknown.

Many mechanisms may potentially contribute to insulin resistance. One major mechanism is the impairment of insulin receptor tyrosine kinase (IR-TK) activity, a key step in insulin receptor signalling. Several inhibitors of IR-TK have been associated to insulin resistance. Among them is PC-1, a class II transmembrane glycoprotein that is overexpressed in tissues of insulin resistant subjects. The human PC-1 gene has been assigned to the same chromosomal region (6q22-q23) where both STS D6S290 (which has been linked to type 2 diabetes in Mexican-Americans), and the gene responsible for transient neonatal diabetes map. The identification and characterization of genetic sequences involved in insulin resistance is of great medical interest.

Database References for Genetic Sequences

The human cDNA and encoded amino acid sequence for PC-1 may be accessed in Genbank, M57736 J05654. As a reference, the "K" allele is provided herein as SEQ ID NO:1, and the encoded polypeptide as SEQ ID NO:2. The "Q" allele is provided as SEQ ID NO:3, and the encoded polypeptide as SEQ ID NO:4.

SUMMARY OF THE INVENTION

Human PC-1 nucleic acids and polypeptides are provided, including promoter and intron-exon boundaries. Polymorphic sequences are provided that encode a form of the protein associated with increased insulin resistance, where a naturally occurring polymorphism of interest comprises a lys→glu substitution at position 121 of the protein, in the high cysteine region. Also provided are polymorphisms in the 3' untranslated region of PC-1. The subject nucleic acids and fragments thereof, encoded polypeptides, and antibodies specific for the polymorphic amino acid sequence are useful in determining a genetic predisposition to insulin resistance. The encoded protein is useful in drug screening for compositions that affect the activity of PC-1 and insulin receptor activity or expression. Screening methods that analyze plasma levels of soluble PC-1 are also provided, where convenient quantitation of PC-1 content is used in diagnosis of insulin resistance.

DESCRIPTION OF THE SPECIFIC EMBODIMENTS

Figure 1A:
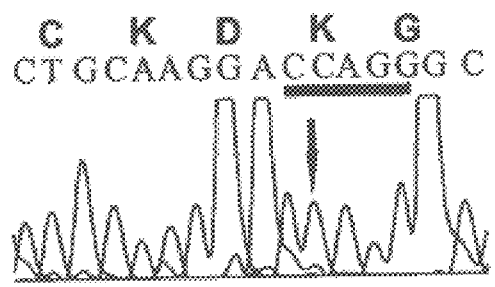
FIGS. 1A and 1B. Sequence analysis of PC-1 exon 4. Arrows point to nucleotide N. The Q allele sequence is depicted in the upper panel, the K allele in the lower. The AvaII restriction enzyme recognition site is underlined in the Q allele sequence. AvaII digestion of PC-1 exon 4 amplimers from 7 different genomic DNAs. The 238 bp amplimer is completely digested in the QQ sample, resulting two smaller 148 and 90 bp fragments. While KK samples remain undigested, KQ samples reveal a partial (50%) digestion.

Methods and compositions are provided for diagnosing a predisposition to human insulin resistance. The methods comprise an analysis of germline DNA for a predisposing polymorphism in the gene encoding PC-1, where presence of the altered gene confers an increased susceptibility to insulin resistance. Human PC-1 gene and gene product compositions are provided that encode specific polymorphic forms of PC-1. Polymorphisms of interest include a coding change at position 121 of the protein, and polymorphisms of the 3' UTR.

In another embodiment of the invention, the concentration of soluble PC-1 protein in patient plasma is used as a diagnostic. PC-1 circulates in human plasma and low plasma PC-1 level is independently associated with several features of the insulin resistant "metabolic syndrome" including abdominal fat distribution, high blood pressure and, with respect to lipid metabolism, insulin resistance.

PC-1 is a class II membrane glycoprotein that inhibits activation of insulin receptor tyrosine kinase, and is associated with insulin resistance. A novel polymorphism in exon 4 of the PC-1 gene is significantly correlated with insulin resistance. The subject genes and fragments thereof, encoded protein, and antibodies specific for the insulin resistance associated forms of PC-1 are useful in characterizing patients for susceptibility to insulin resistance. Such screening methods may be used in conjunction with counseling and preventive measures.

Nucleic Acid Compositions

As used herein, the term PC-1 genes and encoded polypeptides shall be used to generally designate any of the mammalian PC-1 genes and gene products, and unless otherwise stated will be the human homolog. The sequences of the invention comprise a sequence polymorphism, generally resulting in a change in coding sequence, that confer a susceptibility to insulin resistance, and may lead to hyperglycemia and NIDDM. Such polymorphisms may be generically referred to herein as a resistance associated PC-1 sequence, or PC-$1^R$. Counseling and preventive measures are particularly important for such patients, and early diagnosis provides information concerning such a predisposition.

The effect of a candidate sequence polymorphism on PC-1 expression or function may be determined by kindred analysis for segregation of the sequence variation with the disease phenotype, e.g. insulin resistance, hyperglycemia, etc. A predisposing mutation will segregate with incidence of the disease. The subject mutations generally have a dominant phenotype, where a single altered allele will confer disease susceptibility. The penetrance will vary with the specific mutation.

As an alternative to kindred studies, biochemical studies are performed to determine whether a candidate sequence variation in the PC-1 coding region or control regions affects the quantity or function of the protein. The effect of a sequence variation on the interaction between PC-1 and insulin receptor or other tyrosine kinases is determined by binding studies or kinase assays, where a decreased level of inhibition or binding is indicative of a predisposing mutation. Normal PC-1 will inhibit the tyrosine kinase activity of the insulin receptor, but not other tyrosine kinases.

In one embodiment of the invention, polymorphisms of interest provide for amino acid substitutions in the extracellular domain of PC-1, particularly the cysteine-rich domain, which may substitute a charged amino acid with a neutral amino acid. In one embodiment of the invention the amino acid substitution is at a lysine residue in this region, e.g. K121 or K119. Polymorphisms at these residues, where the lysine is substituted with any of the other 19 naturally occurring amino acids, may be referred to generically as a [*121] PC-1 or [*119] PC-1 polymorphisms. Specific polymorphisms of interest substitute a neutral amino acid in place of the lysine, particularly glutamine or arginine. A naturally occurring polymorphism associated with insulin resistance comprises a lys→glu substitution at position 121 of the protein, herein referred to as "[K121Q] PC-1", or merely "[Q] PC-1".

The human [Q] PC-1 amino acid sequence is provided as SEQ ID NO:4, and the encoding gene as SEQ ID NO:3. In order to identify the subject PC-1 polymorphisms, exonic primers from the published sequence data were used to isolate genomic clones. Sequence data from the genomic clones was used to generate specific primers. These primers were used to amplify genomic DNA. The PCR products were screened for mutations using single strand conformation polymorphism (SSCP) analysis. The specific polymorphism found in SEQ ID NO:3 was identified in a number of patients.

DNA encoding a PC-1$^R$ protein may be cDNA or genomic DNA or a fragment thereof that encompasses the altered residue, e.g. [*121] PC-1. As known in the art, cDNA sequences have the arrangement of exons found in processed mRNA, forming a continuous open reading frame, while genomic sequences may have introns interrupting the open reading frame. The term "[*121] PC-1 gene" shall be intended to mean the open reading frame encoding such specific PC-1 polypeptides, as well as adjacent 5' and 3' non-coding nucleotide sequences involved in the regulation of expression, up to about 1 kb beyond the coding region, in either direction. The intron-exon boundaries of the PC-1 gene are provided in the examples.

Genomic sequences of interest comprise the nucleic acids present between the initiation codon and the stop codon, including all of the introns that are normally present in a native chromosome. It may include the 3' and 5' untranslated regions found in the mature mRNA. It may further include specific transcriptional and translational regulatory sequences, such as promoters, enhancers, etc., including about 1 kb of flanking genomic DNA at either the 5' or 3' end of the coding region. The genomic DNA may be isolated as a fragment of 50 kbp or smaller; and substantially free of flanking chromosomal sequence.

The genomic PC-1 5' and 5' sequence, including specific transcriptional and translational regulatory sequences, such as promoters, enhancers, etc., including about 1 kb, but possibly more, of flanking genomic DNA at the 5' end of the transcribed region, is of particular interest. The promoter region is useful for determining the pattern of PC-1 expression, e.g. induction and inhibition of expression in various tissues, and for providing promoters that mimic these native patterns of expression. A polymorphic PC-1 regulatory sequence, i.e. including one or more of the provided 3' UTR polymorphisms, is useful for expression studies to determine the effect of sequence variations on mRNA expression and stability. The polymorphisms are also used as single nucleotide polymorphisms to detect genetic linkage to phenotypic variation in activity and expression of PC-1. The polymorphic 3' UTR sequences are provided as SEQ ID NO:6 ("A" allele); SEQ ID NO:7 (" P" allele); and SEQ ID NO:8 ("N" allele). The polymorphisms are as follows:

| nucleotide position | 127 | 136 | 178 |
| --- | --- | --- | --- |
| SEQ ID NO: 6 | G | G | C |
| SEQ ID NO: 7 | A | C | T |
| SEQ ID NO: 8 | A | G | T |

The promoter region of PC-1 is provided as SEQ ID NO:5. The promoter region is useful for determining natural patterns of expression, particularly those that may be associated with disease. Alternatively, mutations may be introduced into the promoter region to determine the effect of altering expression in experimentally defined systems. The promoter also finds use in the construction of animal models where it is desirable to mimic the native patterns of PC-1 expression. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1: 194–205; Mortlock et al. (1996) *Genome Res.* 6: 327–33; and Joulin and Richard-Foy (1995) *Eur J Biochem* 232: 620–626. Specific regulatory motifs are found in the provided promoter sequence at positions: SEQ ID NO:5; 192–205; and SEQ ID NO:5, 453–458.

The nucleic acid compositions of the subject invention encode all or a part of the subject polypeptides. Fragments may be obtained of the DNA sequence by chemically synthesizing oligonucleotides in accordance with conventional methods, by restriction enzyme digestion, by PCR amplification, etc. For the most part, DNA fragments will be at least about 25 nt in length, usually at least about 30 nt, more usually at least about 50 nt. For use in amplification reactions, such as PCR, a pair of primers will be used. The exact composition of the primer sequences is not critical to the invention, but for most applications the primers will hybridize to the subject sequence under stringent conditions, as known in the art. It is preferable to chose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other. Amplification primers of interest include the intron sequences flanking each exon, as shown in the examples, which may lie immediately outside of the coding sequence, or may span the actual junction. Use of such primers allows specific amplification of the exon sequence from genomic DNA.

The subject PC-1$^R$ genes and associated sequences are isolated and obtained in substantial purity, generally as other than an intact mammalian chromosome. Usually, the DNA will be obtained substantially free of other nucleic acid sequences that do not include a PC-1 sequence or fragment thereof, generally being at least about 50%, usually at least about 90% pure and are typically "recombinant", i.e. flanked by one or more nucleotides with which it is not normally associated on a naturally occurring chromosome.

PC-1 Polypeptides

The subject nucleic acid compositions may be employed for producing PC-1$^R$ protein, or fragments thereof that encompass a polymorphisms of interest, e.g. [Q121] PC-1. For expression, an expression cassette may be employed, providing for a transcriptional and translational initiation region, which may be inducible or constitutive, the coding region under the transcriptional control of the transcriptional initiation region, and a transcriptional and translational termination region. Various transcriptional initiation regions may be employed which are functional in the expression host.

The peptide may be expressed in prokaryotes or eukaryotes in accordance with conventional ways, depending upon the purpose for expression. For large scale production of the protein, a unicellular organism or cells of a higher organism, e.g. eukaryotes such as vertebrates, particularly mammals, may be used as the expression host, such as *E. coli, B, subtilis, S. cerevisiae*, and the like. In many situations, it may be desirable to express the subject PC-1 gene in a mammalian host, whereby the PC-1 gene product will be glycosylated, and secreted.

With the availability of the protein in large amounts by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. By pure is intended free of other proteins, as well as of cellular debris.

The polypeptide is used for the production of antibodies, where short fragments provide for antibodies specific for the particular polypeptide, and larger fragments allow for the production of antibodies over the surface of the protein. Antibodies may be raised to the normal or insulin resistant forms of PC-1. Of particular interest are antibodies that specifically recognize the insulin resistant forms of the protein, i.e. the antibodies do not bind to the normal form. Also of interest are antibodies that recognize the soluble forms of the protein. Antibodies may be raised to isolated peptides corresponding to these mutations, or to the native protein, e.g. by immunization with cells expressing PC-1, immunization with liposomes containing PC-1, etc. Such antibodies are useful in therapy and diagnosis.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the splenocytes immortalized, and then screened for high affinity antibody binding. The immortalized cells, e.g. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage display libraries, usually in conjunction with in vitro affinity maturation.

Phenotypic Indications

Insulin resistance is an essential feature of a great variety of clinical disorders in addition to diabetes, including coronary artery disease, hyperlipidemia, obesity and hypertension. Individuals with non-insulin dependent diabetes have insulin resistance in peripheral tissues. They have a subnormal glucose utilization in skeletal muscle, where glucose transport across the cell membrane of skeletal muscle is the rate limiting step in glucose metabolism. In adipose and muscle cells, insulin stimulates a rapid and dramatic increase in glucose uptake, primarily by promoting the redistribution of the GLUT4 glucose transporter from its intracellular storage site to the plasma membrane. Impaired glucose tolerance (IGT) is associated with a normal fasting blood glucose but an elevated postprandial blood sugar between 7.8 and 11 mmol/L (140 and 199 mg/dL). Some patients with IGT are hyperinsulinimic, and progress to NIDDM.

The response to insulin has been measured by a number of different methods, and insulin resistance has been quantified by a number of different indices. A variety of procedures have been developed to detect the presence of insulin resistance. Using any of these techniques, there is a wide range of insulin sensitivity in normal individuals, some of whose values overlap with similar values in people with diabetes. Therefore, one cannot distinguish between nondiabetic and diabetic individuals on the basis of measures of insulin resistance.

The most widely accepted research method or 'gold standard' is the euglycemic insulin clamp technique. With this procedure, exogenous insulin is infused, so as to maintain a constant plasma insulin level above fasting, while glucose is fixed at a basal level by infusing glucose at varying rates. This glucose infusion is delivered via an indwelling catheter at a rate based on plasma glucose measurements every 5 min. When the plasma glucose level falls below basal, the glucose infusion rate is increased to return plasma glucose to basal levels and vice versa. The amount of glucose infused over time (M value) is an index of insulin action on glucose metabolism. The more glucose that has to be infused per unit time, then the more sensitive the patient is to insulin. Conversely, the insulin-resistant patient requires much less glucose to maintain basal plasma glucose levels. The effect of insulin on fuel metabolism can be assessed in the absence of the confounding effects of hypoglycemic counterregulation, endogenous insulin secretion, or variable levels of hyperglycemia, and multiple insulin actions can be assessed by using isotopes, including regulation of glucose uptake and production, inhibition of lipolysis, and changes in protein metabolism.

An alternative is the minimal model. With this procedure, glucose and insulin are sampled frequently from an indwelling catheter during an intravenous glucose tolerance test; the results are entered into a computer model, which generates a value that is an index of insulin sensitivity (called Si). The acute insulin release (AIR) in response to glucose is also determined by the test. This measure of insulin resistance correlates reasonably well with the euglycemic insulin clamp in nondiabetic subjects. Its accuracy deteriorates in diabetes because the immediate plasma insulin response to the glucose challenge is diminished. Therefore, additional maneuvers are needed to raise plasma insulin levels, such as giving tolbutamide or exogenous insulin in the course of the test.

The most practical way of assessing insulin resistance is the homeostasis model assessment (HOMAIR), involving fasting insulin and glucose levels. This value is calculated as fasting plasma insulin ($\mu$/ml)×fasting plasma glucose (mmol/L)/22.5 (Matthews et al. (1985) *Diabetologia.* 28:412–9). The steady-state basal plasma glucose and insulin concentrations are determined by their interaction in a feedback loop. A computer-solved model is been used to predict the homeostatic concentrations which arise from varying degrees beta-cell deficiency and insulin resistance. Comparison of a patient's fasting values with the model's predictions allows a quantitative assessment of the contributions of insulin resistance and deficient beta-cell function to the fasting hyperglycaemia. The estimate of insulin resistance obtained by homeostasis model assessment correlates with estimates obtained by use of the euglycaemic clamp, the fasting insulin concentration, and the hyperglycaemic clamp. The lower limit of the top quintile of HOMA(IR) distribution (i.e. 2.77) in nonobese subjects with no metabolic disorders has been chosen as the threshold for insulin resistance in some studies (Bonora et al. (1998) *Diabetes* 47:1643–9). The results of this study documented that 1) in hypertriglyceridemia and a low HDL cholesterol state, insulin resistance is as common as in NIDDM, whereas it is less frequent in hypercholesterolemia, hyperuricemia, and hypertension; 2) the vast majority of subjects with multiple metabolic disorders are insulin resistant; 3) in isolated hypercholesterolemia, hyperuricemia, or hypertension, insulin resistance is not more frequent than can be expected by chance alone; and 4) in the general population, insulin resistance can be found even in the absence of any major metabolic disorders.

The measurement of insulin concentration can be done in the overnight fasted condition, since in the postprandial state, glucose levels are changing rapidly and the variable levels of glucose confound the simultaneous measure of insulin levels as an index of insulin action. There is a significant correlation between fasting insulin levels and insulin action as measured by the clamp technique. Very high plasma insulin values in the setting of normal glucose levels are very likely to reflect insulin resistance. As individuals develop diabetes, plasma glucose increases and plasma insulin decreases and so the plasma insulin level no longer reflects only insulin resistance because it becomes influenced by the appearance of a β-cell defect and hyperglycemia.

Detection of PC-1 Associated Insulin Resistance

DNA from a patient having insulin resistance, as described above, suspected of association with aberrant PC-1 is analyzed for the presence of an IR polymorphism. Genetic characterization analyzes DNA or RNA, from any source, e.g. skin, cheek scrapings, blood samples, etc. The nucleic acids are screened for the presence of an insulin resistant polymorphism, e.g. SEQ ID NO:3, as compared to a normal sequence (SEQ ID NO:1, SEQ ID NO:2).

A number of methods are available for analyzing nucleic acids for the presence or absence of a specific sequence. Where large amounts of DNA are available, genomic DNA is used directly. Analysis of genomic DNA may use whole chromosomes or fractionated DNA, e.g. Southern blots, etc. Comparative Genomic Hybridization (CGH), as described in U.S. Pat. No. 5,665,549, provides methods for determining the relative number of copies of a genomic sequence. The intensity of the signals from each labeled subject nucleic acid and/or the differences in the ratios between different signals from the labeled subject nucleic acid sequences are compared to determine the relative copy numbers of the nucleic acid sequences as a function of position along the reference chromosome spread. Other methods for fluorescence in situ hybridization are known in the art, for a review, see Fox et al. (1995) Clin Chem 41(11):1554–1559.

Alternatively, the region of interest is cloned into a suitable vector and grown in sufficient quantity for analysis. Cells that express PC-1 may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985) Science 239:487, and a review of techniques may be found in Sambrook, et al. Molecular Cloning: A Laboratory Manual, CSH Press 1989, pp.14.2–14.33. Alternatively, various methods are known in the art that utilize oligonucleotide ligation as a means of detecting polymorphisms, for examples see Riley et al. (1990) N.A.R. 18:2887–2890; and Delahunty et al. (1996)Am. J. Hum. Genet. 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. genomic DNA, amplification product or cloned fragment, is analyzed by one of a number of methods known in the art. The nucleic acid may be sequenced by dideoxy or other methods, and the sequence of bases compared to a wild-type PC-1 sequence. Hybridization with the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility.

Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels. The [Q] PC-1 allele has an AvaII site that is not present in the [K] PC-1 allele, and this difference may be exploited for genetic screening.

Changes in the promoter or enhancer sequence that may affect expression levels of PC-1 can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

Diagnostic screening may also be performed for polymorphisms that are genetically linked to a predisposition for PC-1 associated insulin resistance, particularly through the use of microsatellite markers, e.g. the variable repeat in intron 3, or single nucleotide polymorphisms, e.g. the 3' UTR polymorphisms. Frequently the microsatellite polymorphism itself is not phenotypically expressed, but is linked to sequences that result in a disease predisposition. However, in some cases the microsatellite sequence itself may affect gene expression. Microsatellite linkage analysis may be performed alone, or in combination with direct detection of polymorphisms, as described above. The use of microsatellite markers for genotyping is well documented. For examples, see Mansfield et al. (1994) Genomics 24:225–233; Ziegle et al. (1992) Genomics 14:1026–1031; Dib et al., supra.

Microsatellite loci that are useful in the subject methods have the general formula:

$$U(R)_nU',$$

where U and U' are non-repetitive flanking sequences that uniquely identify the particular locus, R is a repeat motif, and n is the number of repeats. The repeat motif is at least 2 nucleotides in length, up to 7, usually 2–4 nucleotides in length. Repeats can be simple or complex. The flanking sequences U and U' uniquely identify the microsatellite locus within the human genome. U and U' are at least about 18 nucleotides in length, and may extend several hundred bases up to about 1 kb on either side of the repeat. Within U and U', sequences are selected for amplification primers. The exact composition of the primer sequences are not critical to the invention, but they must hybridize to the flanking sequences U and U', respectively, under stringent conditions. Criteria for selection of amplification primers are as previously discussed. To maximize the resolution of size differences at the locus, it is preferable to chose a primer sequence that is close to the repeat sequence, such that the total amplification product is between 100–500 nucleotides in length.

The number of repeats at a specific locus, n, is polymorphic in a population, thereby generating individual differences in the length of DNA that lies between the amplification primers. The number will vary from at least 1 repeat to as many as about 100 repeats or more.

The primers are used to amplify the region of genomic DNA that contains the repeats. Conveniently, a detectable label will be included in the amplification reaction, as previously described. Multiplex amplification may be performed in which several sets of primers are combined in the same reaction tube. This is particularly advantageous when limited amounts of sample DNA are available for analysis. Conveniently, each of the sets of primers is labeled with a different fluorochrome.

After amplification, the products are size fractionated. Fractionation may be performed by gel electrophoresis, particularly denaturing acrylamide or agarose gels. A convenient system uses denaturing polyacrylamide gels in combination with an automated DNA sequencer, see Hunkapillar et al. (1991) *Science* 254:59–74. The automated sequencer is particularly useful with multiplex amplification or pooled products of separate PCR reactions. Capillary electrophoresis may also be used for fractionation. A review of capillary electrophoresis may be found in Landers, et al. (1993) BioTechniques 14:98–111. The size of the amplification product is proportional to the number of repeats (n) that are present at the locus specified by the primers. The size will be polymorphic in the population, and is therefore an allelic marker for that locus.

Screening for polymorphisms in PC-1 may be based on the functional or antigenic characteristics of the protein. Protein truncation assays are useful in detecting deletions that may affect the biological activity of the protein. Various immunoassays designed to detect polymorphisms in PC-1 proteins may be used in screening. Where many diverse genetic mutations lead to a particular disease phenotype, functional protein assays have proven to be effective screening tools, for example by detecting the specific phosphatase activity on a PC-1 substrate. Alternatively, changes in electrophoretic mobility may be used.

Antibodies specific for an PC-1$^R$ polymorphism may be used in staining or in immunoassays. Samples, as used herein, include cells, e.g. biopsy samples, biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or PC-1$^R$ in patient cells. For example, detection may utilize staining of cells or histological sections, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. flourescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and polymorphic PC-1$^R$ in a lysate. Measuring the concentration of PC-1$^R$ binding in a sample or fraction thereof may be accomplished by a variety of specific assays. A conventional sandwich type assay may be used. For example, a sandwich assay may first attach PC-1$^R$ specific antibodies to an insoluble surface or support. Patient sample lysates are then added to the supports (for example, separate wells of a microtiter plate) containing antibodies. Preferably, a series of standards, containing known concentrations of normal and/or PC-1$^R$ is assayed in parallel with the samples or aliquots thereof to serve as controls. The quantitation may then be performed by adding a labeled antibody specific for PC-1$^R$. Other immunoassays are known in the art and may find use as diagnostics. Ouchterlony plates provide a simple determination of antibody binding. Western blots may be performed on protein gels or protein spots on filters, using a detection system specific for PC-1 as desired, conveniently using a labeling method as described for the sandwich assay.

Immunoassays may also be used in the detection of soluble PC-1 in the plasma of a patient, where quantitative and qualitative analysis may be performed. It is found that decreased levels of PC-1 in the plasma are associated with increased levels in the muscle, therefore a relatively low titer is associated with insulin resistance. In addition, the soluble PC-1 may be analyzed for the presence of a predisposing polymorphism, e.g. that Q121 protein.

A kit may be provided for practice of the subject diagnostic methods. Such a kit may contain hybridization probes that bind to a polymorphic PC-1$^R$ sequence under hybridization conditions where the probe does not bind to a wild type PC-1 sequence. Alternatively, antibodies specific for a polymorphic PC-1$^R$ polypeptide may be included. Such a kit will typically include positive and negative nucleic acid or polypeptide controls, and such other buffers and reagents as may be necessary to practice the method.

Modulation of Gene Expression

The PC-1 genes, gene fragments, or the encoded protein or protein fragments are useful in gene therapy to treat disorders associated with PC-1 insulin resistance. Expression vectors may be used to introduce a PC-1 gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or PC-1 protein may be introduced into tissues or host cells by any number of routes, including viral infection, microinjection, or fusion of vesicles. Jet injection may also be used for intramuscular administration, as described by Furth et al. (1992) *Anal Biochem* 205:365–368. The DNA may be coated onto gold microparticles, and delivered intradermally by a particle bombardment device, or "gene gun" as described in the literature (see, for example, Tang et al. (1992) *Nature* 356:152–154), where gold microprojectiles are coated with PC-1 protein or nucleic acids encoding PC-1, then bombarded into skin cells.

Antisense molecules can be used to down-regulate expression of PC-1 in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840–844).

A specific region or regions of the endogenous sense strand mRNA sequence is chosen to be complemented by the antisense sequence, preferably encompassing the [Q121] PC-1 mutation. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The a-anomer of deoxyribose may be used, where the base is inverted with respect to the natural b-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The antisense molecules and/or other inhibitory agents are administered by contact with cells under conditions that permit entry. The molecules may be provided in solution or in any other pharmacologically suitable form for administration, such as a liposome suspension. There are many delivery methods known in the art for enhancing the uptake of nucleic acids by cells. Useful delivery systems include Sendai virus-liposome delivery systems (see Rapaport and Shai (1994) *J. Biol. Chem.* 269:15124–15131), cationic liposomes, polymeric delivery gels or matrices, porous balloon catheters (as disclosed by Shi et al. (1994) *Circulation* 90:955–951; and Shi et al. (1994) *Gene Therapy* 1:408–414), retrovirus expression vectors, and the like.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. Liposomes may be prepared with purified proteins or peptides that mediate fusion of membranes, such as Sendai virus or influenza virus, etc. The lipids may be any useful combination of known liposome forming lipids, including cationic lipids, such as phosphatidylcholine. The remaining lipid will normally be neutral lipids, such as cholesterol, phosphatidyl serine, phosphatidyl glycerol, and the like.

The therapeutic agents are administered at a dose effective to reduce expression level of PC-$1^R$ at least about 50%, more usually at least 80%, and preferably to substantially undetectable levels.

Genetically Modified Cells and Animals

The subject nucleic acids can be used to generate transgenic animals or site specific gene modifications in cell lines. Transgenic animals may be made through homologous recombination. Alternatively, a nucleic acid construct is randomly integrated into the genome. Vectors for stable integration include plasmids, retroviruses and other animal viruses, YACs, and the like. The modified cells or animals are useful in the study of PC-1 function and regulation. A detectable marker, such as lac Z may be introduced into the PC-1 locus, where upregulation of PC-1 expression will result in an easily detected change in phenotype.

DNA constructs for homologous recombination will comprise at least a portion of a polymorphic PC-1$^R$ gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or ES cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. The transgenic animals may be any non-human mammal, such as laboratory animals, domestic animals, etc. The transgenic animals may be used in functional studies, drug screening, etc., e.g. to determine the effect of a candidate drug on insulin resistance.

Drug Screening Assays

Drug screening identifies agents inhibit or otherwise modulate PC-1 function in cells. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions, transporter function, etc.

The term "agent" as used herein describes any molecule, e.g. protein or pharmaceutical, with the capability of altering or mimicking the physiological function of PC-1. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce nonspecific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of insulin resistance or hyperglycemia attributable to a defect in PC-1 function. The compounds may also be used to inhibit PC-1 function in resistance to insulin, etc. The inhibitory agents may be administered in a variety of ways, orally, topically, parenterally e.g. subcutaneously, intraperitoneally, by viral infection, intravascularly, etc. Topical treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

EXAMPLE 1

Polymorphic Variant of PC-1 Associated with Insulin Resistance

Methods

Subjects 127 unrelated, healthy, non obese subjects (body mass index, BMI, <30 Kg/m$^2$) normotensive (blood pressure<140/90 mm Hg), normal glucose tolerant (by OGTT) were studied. Plasma insulin levels were measured before and during an OGTT that was carried out after 8 days on a weight-maintaining diet. Insulin stimulated glucose disposal was carried out in a subgroup of 71 subjects by the euglycaemic, hyperinsulinemic clamp.

Also studied were 132 type 2 diabetic patients (age= 66.5±8.0 yr, 60 male/72 female, BMI=28.9±4.5 Kg/m$^2$) with a strong family history of diabetes (one first degree relative with type 2 diabetes at the minimum). To minimize the possible inclusion of individuals affected by late onset type 1 diabetes, patients were selected on the basis of age of diabetes onset≧45 yrs, BMI≧21 Kg/m$^2$ and no need for insulin therapy.

Informed consent was obtained from participants before entry into the study, which was approved by the local research ethics committee.

Polymorphism Screening

Overlapping cosmid clones containing the PC-1 gene were isolated by screening a human chromosome 6 specific genomic library with human full length PC-1 cDNA. Cosmids were digested with different four base cutter restriction enzymes, blotted and hybridized to oligonucleotides designed on the cDNA sequence. Positive fragments were cloned and automatically sequenced. Intron-exon junctions were deduced comparing genomic and cDNA sequences.

All exon amplimers, obtained using specific oligonucleotides as primers, were analyzed in 40 unrelated and unscreened individuals by Single Strand Conformation Polymorphism (SSCP) which was performed as follows. Amplification reaction products were denatured for 5 minutes at 87° C. in 90% formamide, 20 mM EDTA, 10 mM NaOH. After denaturation samples were chilled on ice, loaded on a native 8%–12% (according to amplimer size) acrylamide (29:1 Acrylamide-Bisacrylamide) gel (0.04×20× 42 cm) in TBE and electrophoresed at 10 W constant power for 13–16 hours at room temperature. After the electrophoresis, gels were treated by silver staining. PCR products showing different migration patterns at SSCP were cloned in a TA-cloning vector (Stratagene) and four clones for each sample were automatically sequenced from both ends.

Exon 4 amplimers were obtained using oligonucleotides 4Fw [SEQ ID NO:9] (5'-ctgtgttcactttggacatgttg-3') and 4Rv [SEQ ID NO:10] (5'gacgttggaagataccaggttg-3') as primers. PCR products were digested using Avail restriction enzyme and run on 12% native polyacrylamide gel for 2 hours at 500V. After the electrophoresis, gels were stained by silver nitrate. On the gel K alleles are displayed as single, uncut, bands of 238 bp, while Q alleles are shown as a doublet of 148 and 90 bp.

One-hundred-sixty unscreened blood donors were genotyped as background population. All genotypings were performed in duplicate for each individual and to prevent observer bias the investigator was unaware of sample origin.

Skin Fibroblast Culture and Insulin Receptor Autophosphorylation

Fibroblast cultures were established from 4-mm forearm skin-punch biopsies. I$^{125}$ insulin binding data were obtained by inhibition-competition studies. IR-TK (receptor autophosphorylation) was determined exposing cells for 10 min to increasing insulin (0–100 nM) concentrations. Cells were then solubilized in 50 mM Hepes buffer, pH 7.6, containing 1% Triton X-100, 1 mM PMSF, 2 mM orthovanadate and 1% BSA and IR-TK determined.

PC-1 Content in Muscle Tissue Specimens

Muscle tissue specimens were obtained from the external oblique muscle at elective abdominal surgery (cholecystectomy) and were immediately frozen in liquid nitrogen. Soluble extracts were prepared from frozen muscle tissue and PC-1 content was measured by a specific ELISA as previously described and normalized for protein content.

Statistical Analysis

Group values are given as mean±SD. Student's t-test or Mann Whitney U test were used to compare mean values of 2 groups. One-way ANOVA and both Student-Newman-Keuls and Bonferroni t-test were used to compare mean values of more than 2 groups. Two-way ANOVA test was used to compare insulin dose-response curves of IR-TK. Chi-square test was used to compare allele frequency.

Results

Figure 1B:
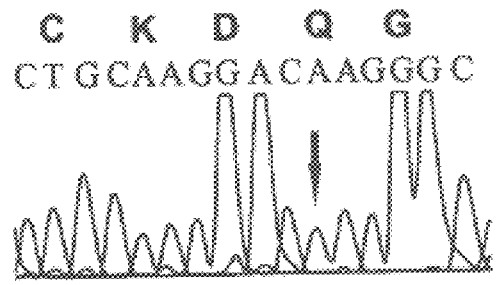
Figure 1B:
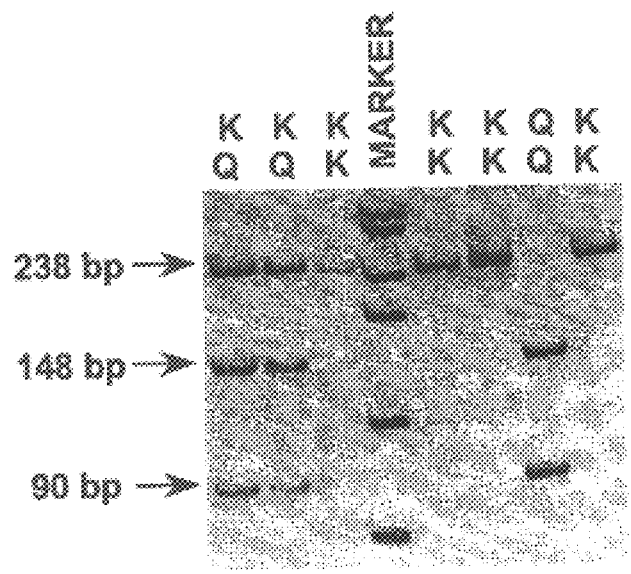

The PC-1 gene has been located on chromosome 6q22–23. Analysis of a YAC contig from the region, allowed it to be more finely mapped, to between markers D6S457 and WI-3398. Only exon 4, which extends from nucleotide 447 to 571 of the cDNA and codes for an extracellular portion of PC-1, showed a polymorphic variant. When screened by SSCP analysis and sequencing it revealed a frequent first position A→C transversion at codon 121 (considering the second in frame ATG as the start codon) (FIG. 1a). This single base change substitutes a glutamine for a lysine in a cysteine-rich region of PC-1 (SEQ ID NO:1 and SEQ ID NO:3, respectively), and creates an AvaII restriction enzyme recognition site. AvaII digestion of exon 4 amplimers cuts the Q allele PCR fragments, leaving the K allele undigested (FIG. 1b). In 160 uncharacterized blood donors, the Q allele frequency was 17.5%, with only 2 QQ homozygotes. The observed genotype frequencies were in agreement with those predicted by the Hardy-Weimberg equilibrium.

Having identified a PC-1 polymorphism which changes both amino acid composition and electric charge, and thus with potential biological relevance, we searched for an association with insulin resistance. Accordingly we studied 127 unrelated, healthy, non obese, normotensive, non diabetic subjects resident in Sicily. As expected, these individuals showed a wide range of plasma insulin levels during OGTT, a finding which in the presence of normal glucose tolerance, indicates a wide range of insulin sensitivity. These data were confirmed by the euglycemic hyperinsulinemic glucose clamp, a more quantitative technique for the measurement of insulin sensitivity. In a subgroup of 71 individuals the M values for insulin stimulated glucose disposal ranged from 2.34 to 9.62 mg/Kg/min.

Figure 2A:
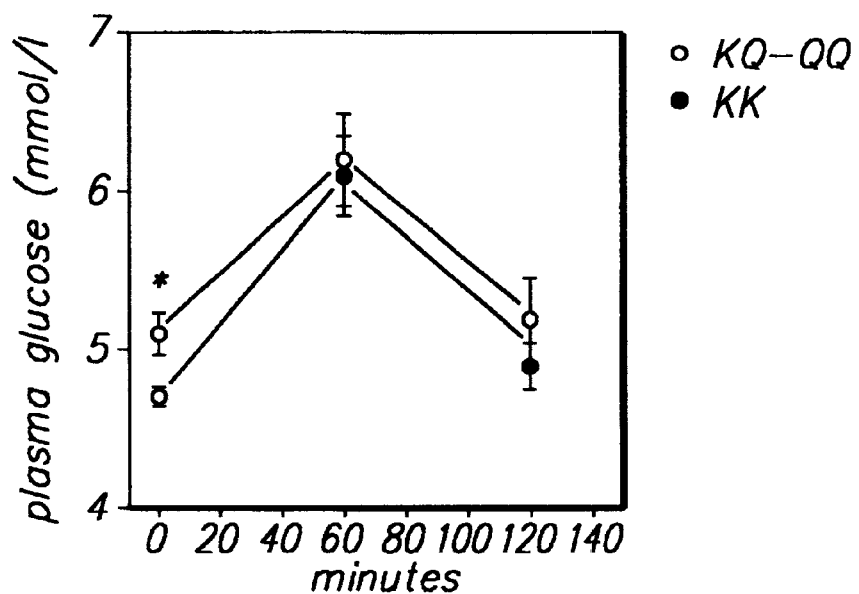
FIGS. 2(A) and 2(B). Plasma glucose (A) and insulin (B) levels during an OGTT (75 g) in Q allele carriers (n=33, white circles) and KK subjects (n=68, black circles). §=p<0.05 and *=p<0.01 vs. KK subjects.
Figure 2B:
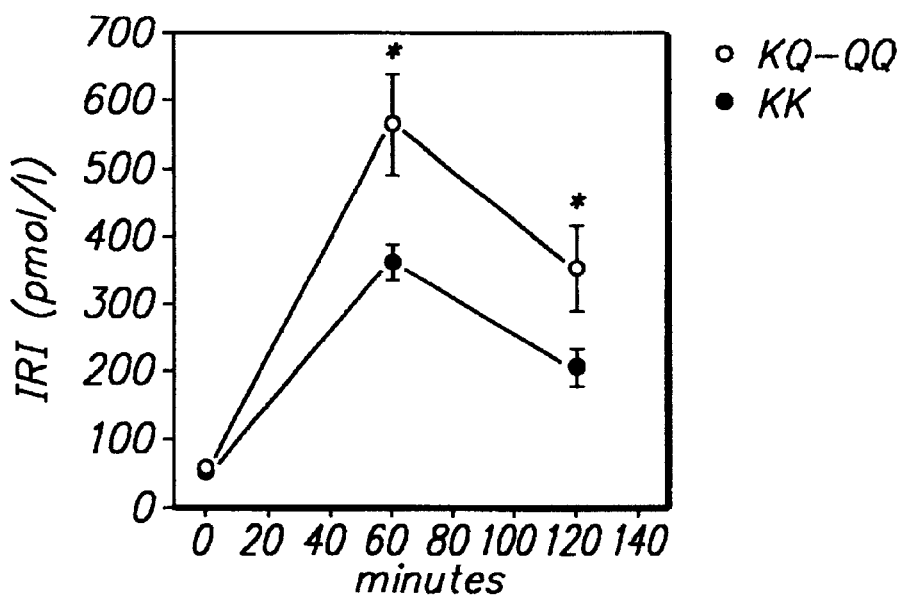

Table 1 summarizes the clinical features of these 2 groups. Q allele carriers showed higher fasting plasma glucose ($p<0.001$) (Table 1 and FIG. 2a) values. They also showed higher plasma insulin values at 60 ($p<0.05$) and 120 ($p<0.01$) minutes during OGTT (FIGS. 2a and 2b).

TABLE 1

Clinical Characteristics of the subject studied

| Genotype | Gender (M/F) | Age (years) | BMI (Kg/m$^2$) | FPG (mmol/l) | FIRI (pmol/l) |
|---|---|---|---|---|---|
| KK (n = 45) | 27/18 | 36.6 ± 2.1 | 23.8 ± 0.5 | 4.7 ± 0.1 | 49.0 ± 4.0 |
| KQ or QQ (n = 22) | 18/4 | 40.3 ± 3.1 | 24.2 ± 0.8 | 5.1 ± 0.1* | 60.0 ± 8.0 |

Data are expressed as mean ± SEM.
*$p < 0.01$ vs. KK subjects
BMI = body mass index
FPG = fasting plasma glucose
FIRI = fasting immunoreactive insulin In the subjects studied by glucose clamp, insulin stimulated glucose disposal was lower in Q allele carriers when compared to KK allele age, sex and BMI matched subjects. No difference was observed in insulin levels at steady state during clamp studies in the 2 groups (485+165 pmol/l vs 460+78). On the average, therefore, Q allele carriers were insulin resistant and maintained normal glucose tolerance due to compensatory hyperinsulinemia. Mean blood pressure, plasma total cholesterol, HDL cholesterol and triglyceride levels were not different between the 2 groups.

Of the 2 subjects with QQ alleles, one was a 35 yr. old male who was studied by euglycemic clamp and had the second lowest M value (M=2.57 mg/Kg/min) of the all the XY males studied. The BMI (28 Kg/m2), blood pressure (138/90 mm Hg), and lipid profile (cholesterol/HDL ratio being 0.16 and triglycerides 176 mg/dl) were in the upper range of the studied individuals. The second QQ subject was a 52 yr. old female with BMI (21 Kg/m2) blood pressure, and her lipid profile was entirely normal. She did not agree to be studied by euglycemic clamp. Both QQ subjects were first degree relatives of a type 2 diabetic patient.

When subjects were subdivided into tertiles according to plasma insulin levels at 120 minutes during the OGTT (tertile 1=low, tertile 2=intermediate, and tertile=3 high insulin levels). As expected, the mean M value for glucose disposal progressively decreased from tertile 1 to tertile 3 (7.22+0.26 mg/Kg/min, n=21 vs. 5.86+0.28, n=25 and 4.89+ 0.23, n=25, $p<0.001$). Q allele frequency was similar in subjects from tertiles 1 and 2 (11.7, n=34 and 10.6%, n=33, respectively), but it was much higher in tertile 3 insulin resistant subjects (29.4%, n=34, $p<0.01$ when compared to the remaining 67 subjects, 11.2%). Also, in 133 type 2 diabetic patients Q allele frequency was higher (20.8%, $p<0.01$) than in tertile 1 and 2 subjects with no difference between obese (BMI>30 Kg/m2, n=90) and non obese (n=42) patients (21.1% and 20.2%, respectively).

TABLE 2

Q allele frequency and insulin sensitivity (M value) in subjects divided in tertiles according to plasma insulin level at 120 min during OGTT (IRI 120 min)

| Tertiles IRI 120 min range | 1 (1353-300 pmole/l) | 2 (273-147 pmol/l) | 3 (140-27 pmol/l) |
|---|---|---|---|
| Q allele frequency % | 29# n = 22 | 15 n = 23 | 9 n = 22 |
| M value (mg/kg/min) | 4.50 ± 0.36* n = 17 | 5.46 ± 0.30** n = 20 | 7.21 ± 0.26 n = 17 |

Data are expressed as mean ± SEM. Number of subjects are given in parenthesis.
$p < 0.05$ vs tertile 3
*$p < 0.01$ vs. tertile 2 and 3
**$p < 0.01$ vs. tertile 3

In order to exclude any association of the Q allele variant with other changes in PC-1, each of the 25 exons from a QQ control were sequenced from the start to the stop codon. No other base change was detected.

Figure 3:
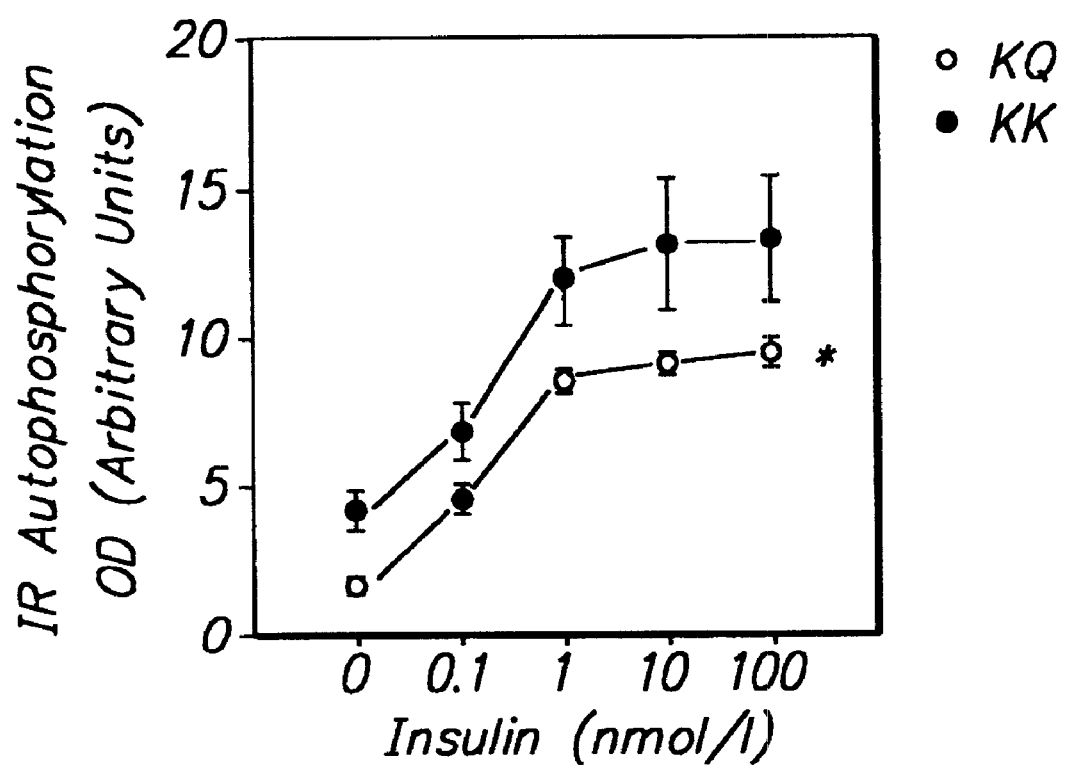
FIG. 3. Insulin receptor autophosphorylation in fibroblasts from Q allele carriers (n=5, white circles) and KK subjects (n=5, black circles). This function was determined by exposing cells for 10 minutes to increasing insulin concentrations (0–100 nM). Cells were then solubilized and the insulin receptor immunocaptured on plastic wells pre-coated with a monoclonal antibody specific to the insulin receptor. After washing, a biotinylated antiphosphotyrosine antibody was added followed by peroxidase-conjugated streptavidin detection assay. Data are expressed as arbitrary units, normalized for protein content. **=p<0.01 vs. KK subjects.

In order to study IR autophosphorylation activity, cultured fibroblasts from 5 Q/K and 5 gender, age and BMI matched KK subjects were selected on the basis of a similar PC-1 protein content (50.3+8.7 and 60.8+15.4 ng/0.1 mg protein, respectively). Q/K fibroblasts showed a reduced IR autophosphorylation activity ($p<0.01$) (FIG. 3). Insulin binding to its receptor was studied and no difference in both total specific binding (% of bound/total radioactivity=0.52+0.10 per 0.1 mg protein and 0.55+0.11 in Q/K and KK subjects, respectively), and IC50(0.27+0.05 nmol/l and 0.26+0.08).

PC-1 content was not significantly different in muscle specimens from 8 QK and 26 KK sex, age and BMI matched subjects (36.5±5.1 ng/mg protein vs. 25.9±2.6 in QK and KK subjects, respectively.

Discussion

The data provided herein demonstrate that a PC-1 gene polymorphism (K121Q in exon 4) is associated with decreased insulin sensitivity in healthy non-diabetic individuals. Because insulin resistance is a major risk factor for the development of type 2 diabetes, Q allele carriers may be at higher risk to develop diabetes. This is supported by the high Q allele frequency observed in patients with type 2 diabetes mellitus. No association was observed with BMI both in healthy and diabetic individuals.

We previously reported that increased PC-1 content in skeletal muscle and adipose tissue is associated with insulin resistance. In addition, when cultured cells overexpress PC-1 they are insulin resistant secondary to both decreased IR tyrosine kinase activity and reduced downstream signaling steps. These latter observations indicate that an increased PC-1 content may play a role in insulin resistance through the inhibition of IR-TK activity.

PC-1 content is not significantly different in skeletal muscle from KQ with respect to KK subjects, indicating that insulin resistance in Q allele subjects is not due to an increased PC-1 protein content. Again, these data suggest that structural differences between the 2 variant proteins may account for different insulin sensitivity, independent of protein content. These data indicate PC-1 is an important candidate for the genetic regulation of whole body insulin sensitivity. PC-1 genotyping can be used for identifying individuals at risk of developing insulin resistance.

EXAMPLE 2

Fasting Plasma PC-1 and its Regulation by Insulin

A soluble form of PC-1 is generated by intracellular cleavage of its transmembrane domain, and subsequently released by the cell. It is not known whether soluble PC-1 circulates in human plasma. The possibility of measuring PC-1 in human plasma would considerably increase the feasibility of screening studies.

A sensitive and specific ELISA was set up, and used to measure plasma PC-1 concentration before and after a 2-hour euglycemic hyperinsulinemic clamp in 22 healthy control, and 27 subjects affected by diseases known to be associated with insulin resistance (i.e. obesity and essential hypertension). The obtained results indicate that low fasting level and abnormal acute regulation by insulin of plasma PC-1 concentration are associated with several features of the "metabolic syndrome", including abdominal fat distribution, high blood pressure and low insulin sensitivity on both glucose and lipid metabolism.

Methods

Plasma PC-1 Measurement

Wells in Maxisorb plates were precoated overnight incubation at 40° C. with an affinity purified polyclonal antibody to PC-1. After washing with TBST buffer (20 mm Tris, 150 mm NaCl, 0.05% Tween-20) to remove unbound antibody, wells were blocked with 150 $\mu$l TBST containing 1% bovine serum albumin (BSA) (30 min at 56° C.), and washed again with TBST. Then, human plasma (10–30 $\mu$l diluted to a total volume of 100 $\mu$l with 50 mM HEPES buffer, pH 7.6, containing 0.05% Tween-20, 1 mM PMSF, 2 mM orthovanadate, 1% BSA and 1 mg/ml bacitracin) was added to each well and PC-1 was allowed to bind overnight at 4° C. After extensive washing with TBST, a biotinylated anti-PC-1 monoclonal antibody was added in the 50 mM HEPES buffer. After 2 hr at 22° C., peroxidase-streptavidin was added and 30 min later, wells were washed again with TBST and then 100 $\mu$l of biotinyl-tyramide solution was added. After 15 min incubation at 22° C., wells were washed with TBST and streptavidin-horseradish peroxidase was added (30 min at 22° C.). After further extensive washing, the peroxidase activity was determined calorimetrically by adding 3.3'.5.5'-tetramethylbenzidine (TMB) at a concentration of 0.4 g/l in an organic base, and measuring the absorbance at 451 nm.

Muscle PC-1 Measurement

Muscle tissue specimens were obtained from the external oblique muscle at elective abdominal surgery (cholecystectomy). After adipose tissue was dissected and blood removed, specimens were immediately frozen in liquid nitrogen. Soluble extracts were prepared from frozen muscle tissue as previously described. Briefly, muscle tissue (approximately 150 mg) was pulverized under liquid nitrogen and then homogenized in 2 ml buffer (50 mm HEPES, 150 mm NaCl, 2 mm PMSF, pH 7.6) at 4° C. using a polytron homogenizer for 10 sec. at medium speed. Triton X-100 was added to a final concentration of 1%, and the homogenates solubilized for 60 min at 4° C. The material was centrifuged at 100K g for 60 min at 4° C. and the supernatants used for the PC-1 content measurement.

Statistical Analysis

One way analysis of variance (ANOVA) was utilized when means values from 3 groups were compared. Paired Student's t test was utilized to compare mean values before and after clamp.

Correlation (either "Pearson" if the data was distributed normally or "Spearman" if the data was not distributed normally) analysis was used to look for numerical relationship between values. Statistically significant correlations were confirmed by linear regression analysis. Stepwise regression analysis was utilized for multiple correlations. Data are given as mean±SEM.

Results

Subjects Studied

Twenty two healthy control and 27 subjects affected by either obesity (BMI>28, n=10) or essential hypertension (mean blood pressure>108 mm Hg, n=12) or both (n=5) were studied. Clinical and metabolic features of the 49 subjects are shown in Table 3. As expected, insulin sensitivity, as indicated by M values derived by euglycemic hyperinsulinemic clamp studies, was significantly reduced in obese and/or hypertensive patients as compared to normal controls.

TABLE 3

| | age | sex | BMI | W/H | MBP | BG | IRI | M |
|---|---|---|---|---|---|---|---|---|
| Control | | | | | | | | |
| mean | 37 | 12/10 | 23.8 | 0.83 | 90 | 5.1 | 65 | 6.2 |
| SEM | 2 | | 0.4 | 0.03 | 2 | 0.1 | 7 | 0.4 |
| Insulin Resistant | | | | | | | | |
| mean | 47 | 19/8 | 29.2 | 0.92 | 109 | 5.3 | 80 | 4.8 |
| SEM | 2 | | 0.8 | 0.02 | 3 | 0.1 | 7 | 0.3 |

Plasma PC-1 Concentration

Fasting plasma PC-1 was measured by ELISA. Human plasma produced a dilution slope that paralleled the PC-1 standard. Intra- and inter-assay coefficient of variations were<8%. Plasma PC-1 concentration ranged from 1 to 70 ng/ml with a mean±S>E>of 26.5±2.9 and a median of 24.5. No significant difference was observed between plasma PC-1 concentration in control (27.7±4.5, n=22) and insulin resistant obese and/or hypertensive (25.6±3.9, n=27) subjects.

When the 49 subjects were considered together, plasma PC-1 concentration was correlated negatively with both waist/hip ratio (−0.49, p=0.001) and systolic blood pressure (−0.36, p=0.016) and positively (0.40, p=0.01) with the ability of insulin to suppress plasma FFA (delta FFA, calculated by subtracting basal FFA from FFA after the two hour euglycemic hyperinsulinemic clamp). Plasma PC-1 concentration remained significantly correlated with the waist/hip ratio also when data were adjusted for BMI and sex (p=0.0024), with systolic blood pressure also when data were adjusted for sex and age (p=0.019) and with delta FFA also when data were adjusted for BMI, sex and waist/hip ratio (p=0.037).

These data demonstrate that PC-1 circulates in human plasma and that low plasma PC-1 level is independently associated with several features of the "metabolic syndrome" including abdominal fat distribution, high blood pressure and, so far as lipid metabolism is concerned, insulin resistance.

Insulin Stimulated Values

In order to verify whether insulin exerts any effect on plasma PC-1, PC-1 was measured after two hour euglycemic hyperinsulinemic clamp. Although the mean plasma PC-1 concentration in the 49 subject after clamp was not different as compared to basal plasma PC-1 level (26.3±3.9, vs. 26.5±4.1), a wide range of the individual effects of insulin infusion were observed, from subjects showing an increase to subjects showing either no change or a reduction in plasma PC-1. When subjects were divided in tertiles according to their whole body insulin sensitivity on glucose values (M values), with the most insulin sensitive in tertile 1 and the most resistant in tertile 3, insulin stimulated PC-1 concentrations were significantly higher than basal plasma PC-1 concentration in subjects from tertile 1 (21.7±5.4 vs.

25.8±5.5 before and after clamp, respectively, p=0.01 5, n=1 6) but not in subjects from tertile 2 (31.7±5.0 vs. 31.9±4.6, n.s., n=17) and 3 (25.9±4.7 vs. 20.7±3.7, n=16). Moreover, the net effect of insulin on plasma PC-1 concentration (delta PC-1, calculated by subtracting basal PC-1 from insulin stimulated PC-1) was positively correlated with M value (0.37, p=0.009) and negatively with BMI (−0.37, p=0.009). A significant (p=0.005) positive correlation between M and delta PC-1 values was observed also when data was adjusted for BMI. A similar correlation between M and delta PC-1 values was observed also when control (0.049, p=0.05, n=22) and insulin resistant obese and/or hypertensive (0.48, p=0.01, n=27) subjects were considered separately).

These data demonstrate that insulin infusion is able to increase plasma PC-1 concentration in the most insulin sensitive subjects and that this effect is blunted in subjects with lower insulin sensitivity.

Plasma v. Muscle Tissue PC-1

In order to verify whether plasma PC-1 concentration was related to PC-1 content in skeletal muscle, we quantified PC-1 in both plasma and biopsied external oblique muscle of 9 additional subjects. PC-1 concentration in plasma was inversely correlated with PC-1 content in muscle (−0.9, p=0.01). These data are compatible with the possibility that the increased PC-1 content previously reported in skeletal muscle of insulin resistant subjects is, at least in part, due to reduction of PC-1 intracellular degradation, and its subsequent release into extracellular fluids, at the level of skeletal muscle tissue.

EXAMPLE 3

Intron/Exon Structure of PC-1

The nucleic acid sequences provided below are the intron-exon boundaries for the human PC-1 gene. It contains all the intron sequences immediately flanking the PC-1 exons. A few bases of the exon 5' and 3' are also provided, which are separated by a "-" sign from the intron, and are further in bold type.

The 3' flanking sequence to exon 2 (i.e. intron 3 at its 5' end) contains a GT repeat that is polymorphic, and provides a marker for genotyping of this locus. The sequences flanking the boundaries or crossing them are useful for specific amplification of the exons.

```
Intron Exon borders
[SEQ ID NO:11] Exon 1
CTCTCGCTG-GTAGGTCCGCGGCCAGGCCCCGGCGCCCGGGAGGGCTGGGAATAC

NGGGAGGGCGGCGCCGAGCTCCTGCGCTCTCAGCGCACTCAGCACCGGGCACGGA

[SEQ ID NO:12] Exon 2
TGAGCTCCACCGGGCCGGCGGCCGCTCTAGAACTAGTGGATCATGCCACTGTACCCTAGCCTGGGTAACAGAGTA

AGACACTATCTCTAAAAATAAAAAATAAGATAAAATATTTTTTAAAAAAGAAACCATGTAATTTTCTCTTTTCTC

CCTACAG-GTATTG...     .AGAAG-GTAATTAGGTGTGTGTGTGTGTGTGTGTGTGTGTGTGTGTATGT

GTGTGCACAGCCTTATTAAGAATGTGATTGAGGTAAACATTATCTCCTATTCCCAAGGGGTAC

[SEQ ID NO:13] Exon 3
AGATTTTTGCCTTACTTTATTACCCCATCTGTATTTTGTAAAGTAGTATTTGAACCTAGTGTACACCTAACTTAG

TTGTATTCGTTGATGTTTACTTTGAATTATATAATGATTAGAAACATCTGACTTATCGTTCAATTTTTTCAG-

TTAA....CCAG-GTAAG

GATGAGCAGGGAAAAAAGTGGAGTTATGGTCATTAGGAAAAGATCCACTAGTTCTAGAGCGGCCGCCACGCCCGG

TGGAGCTT

[SEQ ID NO:14] Exon 4
CGCGGCGGCCGTTCTAGAACTAGTGGATCATACTCACGAAGACAGCAATTCTGTGTTCACTTTGGACATGTTGAA

TTTGAGACATAAAACACATTTTGCTGATGTTTGTTTCTAG-AACATA...GTCAAG-

GTCAGGTGCTCGTTGGGCTCTGCAGCAACCTGGT

ATCTTCCAACCTCTTAACGGGGCTNTACATAAGTGTTATCTTTTATATTAAGANTCATGGCTATTGGGCC

[SEQ ID NO:15] Exon 5
AATCTGTTCACATACTTTGTTTGTGGAATCTGTCTTAATGTGTCTCACAAGCATCACAATTATTATTACTGTTAA

GTGTGTTCATTTTATTTTCTTGAAAATATTTTAG-GT                    GAGAA.....GCAGG-

GTAAGATTATATTCTGAGGTATTAATTTTTTCTTTTTT

AGAAGTACAGCATCATTTTTTTCTTTCCAAATTAAGATGATAAAAATAATAAAATCACTGGTTTATTAAACATTA

CAGGTTGAGTATCCTTTATCCAAAATGTTTGGTATGAGAACTGTTTTGGATTTTGGACTTTTTTGGATTTTGCAA

TATT

[SEQ ID NO:16] Exon 6
CCGCAGCCCGGGGGATCACACAGACCTTAGTGGAAAATCTTCACTGGACCTGTGCCAAGAAGGGGGTACATCTTC
```

-continued

ATTGGATATGTCTTGTCTTTGCTTCTTTAAACATTTTTTTTCTTTTTCATTACCCAG-GTTTG...AAACTAA-

GTGAGTAACTTCAGAG

TTTACTGCTGGAATATCACCATTTCAGTGAGATTGACTAGGCAGGCAGTCTTTCTTGGAAAAGTACTGGCAGAAC

CTAACTGTTTCACTAAACTTTTCTAATGGGCAAAGTAGTTGAACCTTGTGTAgGGCGCCTTATCTTTAATAATGT

GA

[SEQ ID NO:17] Exon 7
TAAGAGAAAAATGAAGTCATCTTTAAGATTGGATTTGTATCCACAGTGTTGCTTTATAATTCATCCTGAATTTTT

ATCTGATTAAAATCCCTCCTGGGTAATTTTTTTTACGTGATTTAGACTGCTGTGGTACCACTGCTAAATGAGGTA

AGCCAATTGTCAGATGTATTTAATAACAATGTTTATTTTTTTCCCTTCTAG-AAAAATGT......TCACC-

GTAAGCTCTGCATTTCAACTTCTATCTGTTTGAAGAAGTGAGATGGGATTGTAACATTTTTTGAGGGAATAGATT

TAAGATAAAAGAAAAACAACTTATTTTCCAATAGGTAGTTAAGTAAGGAAACCCAGGTTCTGATCTTTGCTCTGC

CACAAACTAGCTGTGGCT

[SEQ ID NO:18] Exon 8
ACTACATAAAATCTTAAGAGGTTGCGTTTTGCCATTACCTGATTTTTTTGTTTTTCTTTCCTTAAACTTATTATA

ATTCCATGTAGCTTCAGTTATCGGTTTCTTTTTGATGATTTTTTTCTGTGAATGTATTTAACATTAAGTAAACAC

AACTTGCATATAATCTGT

TTTATCTTTTTTAG-GGATT....AACCA-GTGAGTTCTTTGTTTTTCTACTAA

AATAGTTAATTATTCTCATCTATTTCAATCAGAGTAAAATAACCAGATTCTCTAGAGCTTTTAATAACTGATTTC

ATTTAGTGTGTCTGTGGCCAT

[SEQ ID NO:19] Exon 9
TAATCTCTGACTATTTAATATGTTGTTGCTGCTTAAGAGTCATATTACATGATTATTGTCGTCTAAGTGCTGAAG

CTTGTTGACCTTAAAAGCATTCTAGCACTAGAGAGGAATGCATTGGTGTGGTATGAAAACATACTTTCCTAAGAG

ATGAATGTTGCATGATTTCTTAATTTTCCTTCATTTTCTGCTCCAG-ATTTGG......AATGG-GTATGTG

AAATGAATTTTTTCTAGGATCTGTAATATAGAACAGCTTATTCTTATGTAATGTGGTTTTTATTGAATCCTGAGC

TTTAGCATTTGAGTGATATGTTGGCTGAAAAATGAGAACTGAAGAACTCTTTCTCAAAGAGTTTAGATAGATGGT

AAATGGACAGTAAAACTA

[SEQ ID NO:20] Exon 10
GGGAAAATAAAGTTTTCAAATAAAACCCTTGATTTCAAACACAATAGATGCGAAATAGCATTTACTAGCTCTTAA

TGACATTTTCAATGAAAAAAACTATATTTTACACCCAAACAATTGTCAGCCATCTTTTATTTTTGTTTGTTCTTC

ATTTTAG-TTCAGTA....AGATGAAAG-GTCTGTAGGCAATTAATTTCTATTGTAAATACTTCGTTTTGTA

GAAATGATATACTATTTTCCCCTAGACTACAACAAAACTTTGCTATTTGCTATGATGTTTTATATCGAAATAAAT

TCTTTAGTAAATGATC

[SEQ ID NO:21] Exon 11
GAATTTCAAAGCTGTAAATTAATTTCTCAGTAGAACTGTTACACCAGTGTTATAAAATTAATCCCTATCAATTGA

GGAATTATTTTTTCCATTCTGTTTTTCAATGTGTTCGTAAAATATTACATTTTGATACTGTTTGATTTAG-

ACCACA...CAGTGA[1 -GTAA

GTACATTTTCTCAGTAATTATTTCATTAAACCCAGTCATCGGGCTGAACCTCGCTTTGAAGGAGGCTGCTAGAC

CATTTTATAAGATTCTATCATTTCTGGAAAAAGCAAGTATTATACACAATATTACTAAATATAAGGATGCACTTT

AAACAAAATAAGAGTTGG

[SEQ ID NO:22] Exon 12
GTCTTAGTTTAATGTGAATCAGCTCATTGTAGTTGCATCCACTGGCCCAAATCTATCAATCTGTCGGTCTTTCTT

TCTTTCTTTGTTTCTTTCTTTTTTTTTTTTTTAACAGAGATAGCTTTATGTATAAATAGCCATTAGTGTGGAAG

GTATCACATGAGGTTGTGCTTCCCATTCTTAG-GTCATC.......ATCATG-GTAATCTGAATTTGCATTA

TTTACTCTTCAGGATAAAGGGCTGAAGAAAGTTTACTTGATGGTTTCCCAATTTTTTGTGAATGTTGTAGTTAAT

TCTTTTTTAAAAATGTAGTTTCTTATGGACAGTCTTTAGGAAAAAAATACATTAAATATAAAATATAAGTGAAAC

ACAGAATTCACAGAAACC

[SEQ ID NO:23] Exon 13
GATTTTGAAAAAAGTGAAGTGATAGGTACAGCTGAAATTCTGTCTTACCTATCAGATCTTCAACTAATATGAGTG

CTACACCCATGTTTAACGAATTTAACCTTGGAAGTGAAAGAAGTTCTGCTCTGCATATTAAATTTTTTGTTAAAG

TTACAGCATGTTTTGGGATTTTTTTTTTCTCCTAG-GCATGG.....TACTATTCAT-GTAAGTATATCTC

TGTGATAACTTTGAATATGGTCATATTAAGAATACCTTCCTTTAGGCCGGGCACAGTGGCTCATGCCTGTAATCG

CAGCACTTTGGGAGGCCAAAGTGGGTGGTCACCTGAGGTCAGGAGTTCGAGACCAGCCTGGCCAACATGGTGAAA

CCCTAAAAATACATATAC

[SEQ ID NO:24] Exon 14
GATCCAAACTCTGCATTTAAATACCAAGGCAGGTTTTAAAGAGTTCATTTAAGTCATTACATTGTAGCCACTGAA

AGGAATTAGACAGACCTTTAGGGATCTGACATTCTATATTTTTGTATTATGTTTTAATATAGTATACAATCAAAC

TATTAATTCTTATGTTTGTTCCCCTCCAG-TTAACTATGAAGGCATTGCCCGAAATCTTTCT-GTGAGTA

TCTTTATTTTCCATTATCTAGTTATTTTTACTTTTGTATAATATATATTGAGAGAAAAGTTTCAGCATCTATTAT

TGGGATTGAAGGATTAGAATATTTTAGTAATCTGGGCCAACATGGAAATGCTGTGTAGTTTAAAGATC

[SEQ ID NO:25] Exon 15
CTGATGAAATGTTTGTGAAAAAAAATTTCATATGAAGTTAGAAAGCAATTTCAAGAAAAGTTGACACTTTTTATA

GATATTAGGGAAATATCTTTCCCTAATAAATATCTTTCCCTAAAAAAGTTGACACTTTTTTAGATATTAGGGAAA

TAATAGTTTTTCTTTGCT

GTTTGCAATTTCAG-TGCCGGG....GCATT-GTAAGTTCTGACAGTCTCCCAG

GTAAACTTAGTCTGATCGGTTAGTGATTCAGGGTAACCATTGGGCCCTTTCTAACAATATTGTTATGTGAAAACT

GTATAAGTATGATTCTCTTCACTCTAACCCAGGATTTCTAATGTCGGCCTATGGATGTTTGAGTTAGATAATTCT

TTGTTGTGGAGAGCTGTC

[SEQ ID NO:26] Exon 16
AAAAGATAGAGGTGACTTCTTAATGCTTTTCAAAGCCAGGTGGTTTTATTTACCGTTGTGTTGGTTTAACAAAAT

AGTTACATACTTTTTAATCAATGAAAATAATGTTATG

ATTATCAATTATGTTTTATGAAAGGACTTTACATTTTTAATTCATATATGTCAACATTAG-GAAT....GCAA-

TCTAAAGAAAAAATGATATGCAAAGTTTTAGACTTGAAAACATACTGTGATTATATGTCTTGAATGAGAATTAAT

GGAACATACTTTCATAAAGCTATTTTTCTTTGAACATTAAAGAATTTTGTTAAAGTTTTATATTCATTGGCTATT

ACTAAAAAGTCAAAAAAC

[SEQ ID NO:27] Exon 17
AAAACTAAGAGACCTATCCTAGATGTCCTTAGATTATGTGTGTGATAGGGTTAAAACTATATTTCCCACAAAGTC

CACTGAGCGTGGTAGTTTTCCTCTTATCTTATCATAACCAGTTTGTATATGTACAATGTGGATAACAGAATTTTT

GGGACCAACTTGTAGACAGCTGAAATGCACTGATAAACTTCCTTTTCTGGCCATCTAG-GCCCT.....GTG

TG-GTAAGTGTGAACAGGTGCCTTTTTTCCCTTCTGAAAATAGACCTGAAATAGGA

TTATCAAAAGCAGGTCACATTGTAGGCAACTTTGTGGAGATGATGGTGAGGCAAGACAGATTTTTACCTTCTTCC

TGACTCTCAGACTCACTGAAGAAATGTGGGGAACATG

[SEQ ID NO:28] Exon 18
CATATCAGTATTTCTATTAAAAATAACCTAGTCTTAAATACTCTAAAACCCAAGAGAGTTTTATACTTTTATTTT

AGTTAAAGAGTAAATGACTCATGTATTTGGTTTTAAAAAAGTAAAGATCATGGCACAAGTCTACTATTTGTTTGA

TTTGAAACATCTAAGTAACTCTACCATCTTGAAATTATGCAG-ATTTA....CTTCG-GTAAGTATCGTCAA

GAAGTTTGGTCCAGTATGTATGGTTTGATAGCACCCTCTGCATAGCATGTGCTGTAAAAATACTTAATAATCAAA

-continued

TTAgAATTTAGGAGTGGGGGTAGGTAAACATATGTTTTAATTCTAGGGGGCGCATGTAAATCTTTTGTGATATAT

CTTTTCTCTTTCTAGTTT

[SEQ ID NO:29] Exon 19
GTGAAAGAGCAACACTCTTGCCTTGAAAGAGAAAAAAAATCCACTAATACAAGACTATCATAAATGATCTTTGT

TTTATGTTGGAATAATCAATCTATAGCGGTCTATGTTACAAAATTTAAAACATGTCTCTCAGTCCTTACAAATAG

TTTTATAACCTTTTTTCAG-ATTTTGCC.....GAAG-GTAAGGCATGCTACACACTCAAGCTCGGAATGTG

AAGCAGGCATTTTCTCATCAGTGTGAAATGCAGAGAACTGGCTTGGGGGTATTATTTGAGAATAACCAATAAAAT

AAAGGGAGTTCTGGAGGACCACCTGATGAAACATAGAGGTTTCTTTGCT

[SEQ ID NO:30] Exon 20
GTCTTCTTAATTGTTTATGCTTGTACCCTTTGTAATCAGTTTTTTAATAGTTAAAAGTAAATCTTCAATATAAT

TAAGTAGAGGAAAGGATTAGATGAGTGTATCACACTATATATTATCATATAATGCACACTAACTACATTTATTTT

CATCCTGTGACCCAAG-A     GAAGATTA....GACAGAAAT-GCAAGTATTTGTCACCTCTTTATGTGTGGCC

ATTTCAAATTAATGATTAAGCAGAACATTAAATGCATAGTTTCTCACTGTTCACCTTGGCTTTATACTCAGTTCC

CGCATTAGAGGAACACTGAAGAGGGAGTCAGAAAAAT

[SEQ ID NO:31] Exon 21
TTTAATATTGTAAAGCATTTTTACACTTTAGTTAGAAAAAAAGATGAATATACTAGTAGGAAAATAGGGAAGGAC

ATGAGCTGACAGCTAGAGCTTCATAATTTTATGATGTAGTTCACCTTTAAATATTAATAAAGCAATTTTCTTCTC

TGTGCCTGATATCTGAGAGTTCTTCTCATTTTCGTTCTTCAG-GACA....CCACCAC-GTAAGTTTTTCC

TCTCCTGACCTTCCCTTTTCTCCTTTTTGTTTCTTTCTTGTTTATAAATCCTACCATACATTATAGGGTAATAT

ATATATTACCTATTATATATATAGCTATATATATATACCTTTGTTTATTTATTGTGA

[SEQ ID NO:32] Exon 22
CTCATCTTGAAAAGACTTCTTAAATATTTTATTTTTGTAAAGGACTTGACCAAACACATAACATTTTCCCTCGAC

CCTGTACTTGGGAAAGTTTTACAGGTTTAAGATGGTACTCAGCTAATTTTTAAAAATGCTCCCCTAACCATGAGA

AAGTATAATTTCCTATGTTATTTGTGAAGAATGAAAAAGTTGTCCTCTTTTCTCTTTGTAG-AACTA....TT

CAAG-GTAAATAATGTTAACTCTATATTTGATAATTTTAATGAATTTGTGCACAT

ATAGGCATAATTCATATGTATAGGACTTATGGTCTAAATTAAATGAATTAATACCAAATACATTCTTAAAGGTTT

AACTTTGAGAATACTAGTACACAAAAATTCTAC

[SEQ ID NO:33] Exon 23
CTGGGTGATATAGCACGACTCTGTCTCTAAACAAAAAACAAAACAAAACGAAGACTGAAGCCAAACTTGACTTTA

TCTTTATTTACTATAAATGCTAATTTTGAATCATGGTGTTAATTTATTTCACACGTCAACATGGTCCCTTGTTCT

TTTGAAACTACACTGGCTTCTATCTTGTTTCAG-TTATA....GAGGCA-GTAAGAACATATTTCATTACTC

TTAAAAATAGGAATTACCATCCAGTAGAAATGGGATTACCATCCAGTTGAGTCAAGAGAACCTTTTTTATCCAGT

GTCGTATGTTTATGTGTATGACACTTCTGACTACACAGGAAGCCTCTTGAAATATCTGATTAATTTTGATGTtTT

GCTCAATGTTCAGTAAAA

[SEQ ID NO:34] Exon 24
GTTCTTATATTTAATTATTGGTTGGAATTTGATTTTATATGTATTAAAAGCATGCTCTACTGAAATATTCATCA

AAAGGAAGATAGTTATTTCTTTCTTAAAATGAATATTGGCATGTTTTACAG-AAAAA....TGTGTG-

GTAAGTAGCTTTTGTATATTTAC

TTTGCATGTTGAAAATCTAGACATATGCATATTTGTTTATGTCACCCATCTGACATTACAGTGAGAGAAAGCACA

ACTGAGTACACATGGACTTCGAAATTATAGGATGCTTTTAAATTTGATCTTTTAAGATGACATATCTTTGGGGAA

GACTACCCTGTCTGCTTT

[SEQ ID NO:35] Exon 25
AATTAAACAAACATGCATGGTATGTATTAGAAGGAAAGCTACTCAAGAGGAGAGATGATGCCTAACAAATCATGT -continued

```
GGCACGTTCCACTTCAGAGCTGAAATCTCGTAAATGATTAAACTGGGGAGATGGAGCACTTATAGAAGTGAACTG

AGTGTTCTCTTGGTAACTTTTCTTTTATATTTCCTATTCTCCTAG-CATGG....ATTAA-AAAAGAAAAA

TATTCCTATCCTGCTCACTGGTAATTAACATAGGTTTAAAATGGCTTCAAATGTGGCCCTATAGACGGTTAAAAT

TGTACCTTATCTTGGCAAAACTTCAGAGCACCAGTCAGTGCATGCAAGGTGCCATTTTTTATTGAGATGCTTAGA

ATGTTTCTTTCTGTGCAC
```

It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. An isolated nucleic acid encoding the amino acid sequence of SEQ ID NO: 4.

2. An isolated oligonucleotide consisting of at least 18 contiguous nucleotides from an isolated nucleic acid encoding SEQ ID NO: 4, wherein said oligonucleotide includes a portion of the nucleic acid sequence that encodes a glutamine at position 121 of SEQ NO: 4.

3. A method for detecting a predisposition to insulin resistance in an individual, the method comprising: analyzing an individual for the presence of a genetic polymorphism in the genomic sequence of a human PC-1 allele, wherein said human PC-1 allele encodes a glutamine amino acid at position 121 of SEQ ID NO:4, and wherein the presence of said glutamine at position 121 of SEQ ID NO: 4 is indicative of a predisposition to insulin resistance.

* * * * *